(12) United States Patent
Nettekoven et al.

(10) Patent No.: US 7,622,466 B2
(45) Date of Patent: Nov. 24, 2009

(54) AZAINDOLE-2-CARBOXAMIDE DERIVATIVES

(75) Inventors: Matthias Nettekoven, Grenzach-Wyhlen (DE); Jean-Marc Plancher, Hagenthal-le-Bas (FR); Hans Richter, Grenzach-Wyhlen (DE); Olivier Roche, Folgensbourg (FR); Sven Taylor, Riedisheim (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/093,669

(22) PCT Filed: Nov. 8, 2006

(86) PCT No.: PCT/EP2006/068206
§ 371 (c)(1),
(2), (4) Date: May 14, 2008

(87) PCT Pub. No.: WO2007/057329
PCT Pub. Date: May 24, 2007

(65) Prior Publication Data
US 2009/0005379 A1   Jan. 1, 2009

(30) Foreign Application Priority Data
Nov. 18, 2005   (EP) .................. 05110949

(51) Int. Cl.
C07D 471/04   (2006.01)
A61K 31/5377   (2006.01)
A61K 31/4353   (2006.01)

(52) U.S. Cl. ............. 514/234.5; 514/300; 546/113

(58) Field of Classification Search .......... 546/113; 514/234.5, 300
See application file for complete search history.

(56) References Cited

U.S. PATENT DOCUMENTS

2004/0224952 A1   11/2004   Cowart et al.

FOREIGN PATENT DOCUMENTS

| WO | WO 96/03400 | 2/1996 |
| WO | WO 04/000831 | 12/2003 |
| WO | 2004101563 | * 11/2004 |
| WO | WO 2005/097740 | 10/2005 |

OTHER PUBLICATIONS

K.M.Brashear et al, Bioorganic and Medicinal Chemistry Letters, vol. 7, No. 21, 1997, pp. 2793-2798 XP002429012 tables 2,3.

* cited by examiner

*Primary Examiner*—D. Margaret Seaman
*Assistant Examiner*—Niloofar Rahmani
(74) *Attorney, Agent, or Firm*—George W. Johnston; Dennis P. Tramaloni; Samuel H. Megerditchian

(57) ABSTRACT

The present invention relates to compounds of formula (I) wherein $R^1$ to $R^5$ are as defined in the description and claims, and pharmaceutically acceptable salts thereof. The compounds are useful for the treatment and/or prevention of diseases which are associated with the modulation of 113 receptors.

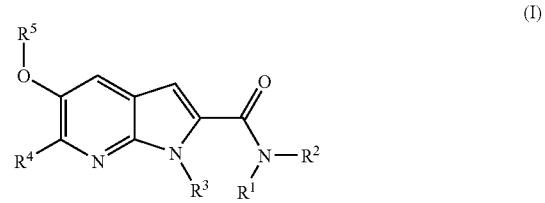

24 Claims, No Drawings

AZAINDOLE-2-CARBOXAMIDE DERIVATIVES

The present invention is concerned with novel azaindole-2-carboxamide derivatives, their manufacture, pharmaceutical compositions containing them and their use as medicaments. The active compounds of the present invention are useful in treating obesity and other disorders.

In particular, the present invention relates to compounds of the general formula

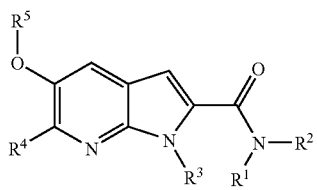

I wherein
$R^1$ is selected from the group consisting of
  lower alkyl, lower alkenyl, lower alkinyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenalkoxy and lower hydroxyalkyl,
  lower phenylalkyl wherein the phenyl ring may be unsubstituted or substituted with one or two groups independently selected from lower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl, and
  lower heterocyclylalkyl wherein the heterocyclyl ring may be unsubstituted or substituted with one or two lower alkyl groups;
$R^2$ is selected from the group consisting of hydrogen,
  lower alkyl, lower alkenyl, lower alkinyl,
  cycloalkyl, lower cycloalkylalkyl,
  lower hydroxyalkyl, lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenalkoxy and lower hydroxyalkyl,
  lower phenylalkyl wherein the phenyl ring may be unsubstituted or substituted with one or two groups independently selected from tower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl, and
  lower heterocyclylalkyl wherein the heterocycyl ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group,
  said saturated or partly unsaturated heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl, or
  being condensed with a phenyl ring, said phenyl ring being unsubstituted or substituted by one, two or three groups independently selected from lower alkyl, lower alkoxy and halogen;
$R^3$ is selected from the group consisting of hydrogen, lower alkyl, lower hydroxyalkyl,
  lower alkoxyalkyl, lower halogenalkyl, lower cycloalkylalkyl,
  lower alkanoyl, lower cyanoalkyl, lower alkylsulfonyl,
  phenylsulfonyl wherein the phenyl ring may be unsubstituted or substituted with one or two groups independently selected from lower alkyl, halogen, lower alkoxy, lower halogenalkoxy and lower hydroxyalkyl;
  phenyl unsubstituted or substituted with one or two groups independently selected from lower alkyl, halogen, lower alkoxy, lower halogenalkoxy and lower hydroxyalkyl;
  lower phenylalkyl, wherein the phenyl ring may be unsubstituted or substituted with one or two groups independently selected from lower alkyl, halogen, lower alkoxy, lower halogenalkoxy and lower hydroxyalkyl; and
  heteroaryl unsubstituted or substituted with one or two groups independently selected from lower alkyl or halogen;
$R^4$ is hydrogen or halogen;
$R^5$ is a group selected from

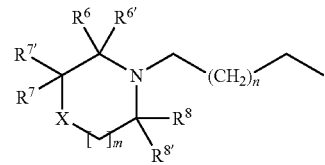
Het 1

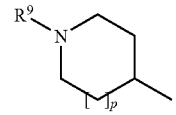
Het 2

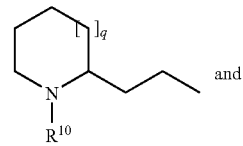
and
Het 3

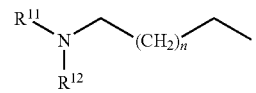
Het 4 wherein
m is 0, 1 or 2;
n is 0, 1 or 2;
X is selected from $CR^{13}R^{13'}$, O and S;

$R^6$, $R^{6'}$, $R^7$, $R^{7'}$, $R^8$, $R^{8'}$, $R^{13}$ and $R^{13'}$ independently from each other are selected from the group consisting of hydrogen, lower alkyl, hydroxy, halogen and dialkylamino, or $R^7$ and $R^{13}$ together form a double bond;

p is 0, 1 or 2;

$R^9$ is selected from lower alkyl, cycloalkyl, lower cycloalkylalkyl and lower phenylalkyl;

q is 0, 1 or 2;

$R^{10}$ is lower alkyl;

$R^{11}$ is lower alkyl;

$R^{12}$ is lower alkyl;

and pharmaceutically acceptable salts thereof.

The compounds of formula I are antagonists and/or inverse agonists at the histamine 3 receptor (H3 receptor).

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Mipatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a II3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of the is receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al: Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinkson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

It is therefore an object of the present invention to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_2$-$C_8$-alkenyl", alone or in combination, signifies a straight-chain or branched hydrocarbon radical comprising an olefinic bond and tip to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-8}$-alkinyl", alone or in combination, signifies a straight-chain or branched hydrocarbon residue comprising a triple bond and up to 8, preferably up to 6, particularly preferred up to 4 carbon atoms. Examples of alkinyl groups are ethinyl, 1-propinyl, or 2-propinyl. A preferred example is 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl, cyclopentyl and cyclohexyl.

The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy.

Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfonylethyl.

The term "alkylsulfonyl" or "lower alkylsulfonyl" refers to the group R'—S(O)$_2$—, wherein R' is lower alkyl and the term "lower alkyl" has the previously given significance. Examples of alkylsufonyl groups are e.g. methylsulfonyl or ethylsulfonyl.

The term "halogen" refers to fluorine, chlorine, bromine and iodine, with fluorine, chlorine and bromine being preferred.

The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkyl" or "hydroxy-$C_{1-8}$alkyl" refers to lower alkyl groups as defined above wherein at least one of the hydrogen atoms of the lower alkyl group is replaced by a hydroxy group. Examples of lower hydroxyalkyl groups are hydro-oxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "carbamoyl" refers to the group CO—NH$_2$.

The term "dialkylcarbamoyl" or "$C_{1-8}$-dialkylcarbamoyl" refers to the group —CO—NR'R" wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group as defined herein before. A preferred lower dialkylcarbamoylalkyl groups is dimethylcarbamoylmethyl.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are furyl and pyridyl.

The term "lower heteroarylalkyl" or "heteroaryl-$C_{1-8}$alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl. A preferred heterocyclyl group is piperidinyl.

The term "lower heterocyclylalkyl" or "heterocyclyl-$C_{1-8}$-alkyl," refers to lower alkyl groups as defined above wherein at least one of the hydrogen atoms of the lower alkyl group is replaced by a heterocyclyl group as defined above.

The term "form a 4-, 5-, 6- or 7-membered saturated heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. A "4-, 5-, 6- or 7-membered saturated or partly unsaturated heterocyclic ring containing a sulfinyl group or a sulfonyl group" means a N-heterocyclic ring that contains a —S(O)— group or a —SO$_2$— group, for example 1-oxothiomorpholinyl or 1,1-dioxothiomorpholinyl. The heterocyclic ring may be unsubstituted or substituted by one, two or three groups independently selected from lower alkyl, lower alkoxy and oxo. The heterocyclic ring may also be condensed with a phenyl ring, said phenyl ring being unsubstituted or substituted by one, two or three groups independently selected from lower alkyl, lover alkoxy and halogen. An example for such a condensed heterocyclic ring is 3,4-dihydro-1H-isoquinoline.

The term "oxo" means that a C-atom of the heterocyclic ring may be substituted by =O, thus meaning that the heterocyclic ring may contain one or more carbonyl (—CO—) groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

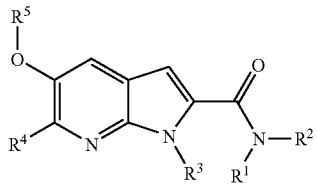

I wherein
$R^1$ is selected from the group consisting of
    lower alkyl, lower alkenyl, lower alkinyl,
    cycloalkyl, lower cycloalkylalkyl,
    lower hydroxyalkyl,
    lower alkoxyalkyl,
    lower alkylsulfanylalkyl,
    lower dialkylaminoalkyl,
    lower dialkylcarbamoylalkyl,
    phenyl unsubstituted or substituted with one or two groups independently selected from lower alkyl, lower halogenalkoxy and lower hydroxyalkyl,
    lower phenylalkyl wherein the phenyl ring may be unsubstituted or substituted with one or two groups independently selected from lower alkyl, halogen, lower alkoxy and lower hydroxyalkyl,
    lower heteroarylalkyl wherein the heteroaryl ring may be unsubstituted or substituted with one or two groups independently selected from lower alkyl, halogen, lower alkoxy and lower hydroxyalkyl, and
    lower heterocyclylalkyl wherein the heterocyclyl ring may be unsubstituted or substituted with one or two lower alkyl groups;
$R^2$ is selected from the group consisting of hydrogen,
    lower alkyl, lower alkenyl, lower alkinyl,
    cycloalkyl, lower cycloalkylalkyl,
    lower hydroxyalkyl, lower alkoxyalkyl,
    lower alkylsulfanylalkyl,
    lower dialkylaminoalkyl,
    lower dialkylcarbamoylalkyl,
    phenyl unsubstituted or substituted with one or two groups independently selected from lower alkyl, lower halogenalkoxy and lower hydroxyalkyl,
    lower phenylalkyl wherein the phenyl ring may be unsubstituted or substituted with one or two groups independently selected from lower alkyl, halogen, lower alkoxy and lower hydroxyalkyl,
    lower heteroarylalkyl wherein the heteroaryl ring may be unsubstituted or substituted with one or two groups independently selected from lower alkyl, halogen, lower alkoxy and lower hydroxyalkyl, and
    lower heterocyclylalkyl wherein the heterocycyl ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group,
    said saturated or partly unsaturated heterocyclic ring
    being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl, or
    being condensed with a phenyl ring, said phenyl ring being unsubstituted or substituted by one, two or three groups independently selected from lower alkyl, lower alkoxy and halogen;
$R^3$ is selected from the group consisting of hydrogen, lower alkyl, lower hydroxyalkyl, lower alkoxyalkyl, lower halogenalkyl, lower cycloalkylalkyl,
    lower alkanoyl, lower cyanoalkyl, lower alkylsulfonyl,
    phenylsulfonyl wherein the phenyl ring may be unsubstituted or substituted with one or two groups independently selected from lower alkyl, halogen, lower alkoxy lower halogenalkoxy and lower hydroxyalkyl;
    phenyl unsubstituted or substituted with one or two groups independently selected from lower alkyl, halogen, lower alkoxy, lower halogenalkoxy and lower hydroxyalkyl; lower phenylalkyl, wherein the phenyl ring may be unsubstituted or substituted with one or two groups independently selected from lower alkyl, halogen, lower alkoxy, lower halogenalkoxy and lower hydroxyalkyl; and
    heteroaryl unsubstituted or substituted with one or two groups independently selected from lower alkyl or halogen;
$R^4$ is hydrogen or halogen;

$R^5$ is a group selected from

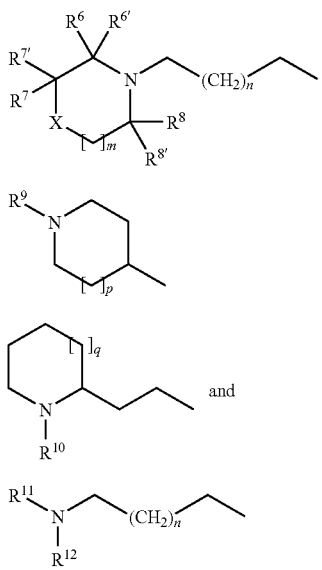

Het 1

Het 2

Het 3 and

Het 4 wherein
m is 0, 1 or 2;
n is 0, 1 or 2;
X is selected from $CR^{13}R^{13'}$, O and S;
$R^6$, $R^{6'}$, $R^7$, $R^{7'}$, $R^8$, $R^{8'}$, $R^{13}$ and $R^{13'}$ independently from each other are selected from the group consisting of hydrogen, lower alkyl, hydroxy, halogen and dialkylamino, or
$R^7$ and $R^{13}$ together form a double bond;
p is 0, 1 or 2;
$R^9$ is selected from lower alkyl, cycloalkyl, lower cycloalkylalkyl and lower phenylalkyl;
q is 0, 1 or 2;
$R^{10}$ is lower alkyl;
$R^{11}$ is lower alkyl:
$R^{12}$ is lower alkyl;

and pharmaceutically acceptable salts thereof.

Preferred compounds of formula I of the present invention are compounds of formula I, wherein
$R^1$ is selected from the group consisting of
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl, lower dialkylcarbamoylalkyl,
phenyl unsubstituted or substituted with one or two groups independently selected from lower alkyl, lower halogenalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl,
lower heteroarylalkyl wherein the heteroaryl ring may be unsubstituted or substituted with one or two groups independently selected from lower alkyl, halogen, lower alkoxy or lower hydroxyalkyl, and
lower heterocyclylalkyl wherein the heterocycyl ring may be unsubstituted or substituted with one or two lower alkyl groups, and
$R^2$ is hydrogen or lower alkyl.

More preferred are compounds of formula I, wherein
$R^1$ is selected from the group consisting of
lower alkyl,
cycloalkyl, lower cycloalkylalkyl,
lower alkoxyalkyl, and
lower phenylalkyl wherein the phenyl ring may be unsubstituted or substituted with one or two groups independently selected from lower alkyl, halogen, lower alkoxy or lower hydroxyalkyl, and
$R^2$ is hydrogen or lower alkyl.

Especially preferred are those compounds of formula I, wherein $R^1$ is lower phenylalkyl wherein the phenyl ring may be unsubstituted or substituted with one or two groups independently selected from lower alkyl, halogen, lower alkoxy or lower hydroxyalkyl, and $R^2$ is hydrogen or lower alkyl.

Also preferred are compounds of formula I, wherein $R^1$ and $R^2$ are lower alkyl.

Furthermore, compounds of formula I according to the present invention are preferred, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group, said saturated or partly unsaturated heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

More preferred are compounds of formula I according to the invention, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two three groups independently selected from lower alkyl, halogen, halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

Even more preferably, $R^1$ and $R^2$ together with the nitrogen atom to which they are attached form a heterocyclic ring selected from the group consisting of morpholine, piperidine, 4,4-difluoropiperidine and pyrrolidine.

Furthermore, compounds of formula I according to the present invention are preferred, wherein $R^3$ is selected from the group consisting of
hydrogen, lower alkyl, lower hydroxyalkyl, lower alkoxyalkyl, lower halogenalkyl,
lower cycloalkylalkyl, lower cyanoalkyl,
lower alkylsulfonyl, and
phenyl unsubstituted or substituted with one or two groups independently selected from lower alkyl, halogen, lower alkoxy, lower halogenalkoxy and lower hydroxyalkyl.

More preferred are those compounds of formula I wherein $R^3$ is selected from the group consisting of hydrogen, lower alkyl, lower halogenalkyl, lower cycloalkylalkyl and lower cyanoalkyl, with those compounds, wherein $R^3$ is hydrogen, being especially preferred.

$R^4$ is hydrogen or halogen. Compounds of formula I, wherein $R^4$ is selected from the group consisting of hydrogen, chloro and bromo, are preferred.

Especially preferred compounds of formula I according to the invention are those, wherein $R^4$ is hydrogen.

Further preferred compounds of formula I according to the present invention are those compounds, wherein $R^5$ signifies

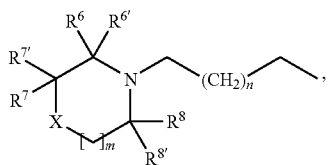
Het 1 wherein m is 0, 1 or 2; n is 0, 1 or 2; X is selected from $CR^{13}R^{13'}$, O and S; and $R^6$, $R^{6'}$, $R^7$, $R^{7'}$, $R^8$, $R^{8'}$, $R^{13}$ and $R^{13'}$ independently from each other are selected from the group consisting of hydrogen, lower alkyl, hydroxy, halogen and dialkylamino, or $R^7$ and $R^{13}$ together form a double bond.

Within this group, those compounds of formula I are preferred, wherein m is 0 or 1, n is 1, X is $CR^{13}R^{13'}$ and $R^6$, $R^{6'}$, $R^7$, $R^{7'}$, $R^8$, $R^{8'}$, $R^{13}$ and $R^{13'}$ are hydrogen or lower alkyl.

Also preferred are compounds of formula I, wherein $R^5$ signifies

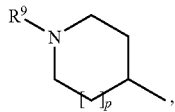
Het 2 wherein p is 0, 1 or 2, and $R^9$ is selected from lower alkyl, cycloalkyl, lower cycloalkylalkyl and lower phenylalkyl.

Within this group, those compounds are preferred, wherein $R^9$ is lower alkyl. Also preferred are compounds, wherein $R^9$ is cycloalkyl. The integer of p is preferably 1.

A further preferred group of compounds of formula I according to the invention are those, wherein $R^5$ signifies

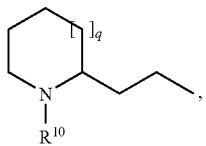
Het 3 wherein q is 0, 1 or 2; and $R^{10}$ is lower alkyl.

Compounds of formula I according to the present invention, wherein $R^5$ signifies

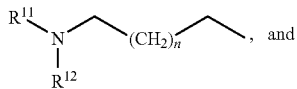
Het 4 wherein n is 0, 1 or 2, $R^{11}$ is lower alkyl and $R^{12}$ is lower alkyl, are also preferred.

Examples of preferred compounds of formula I are the following:

morpholin-4-yl-[5-(3-piperidin-1-yl-propoxy)-1H-pyrrolo [2,3-b]pyridin-2-yl]-methanone, piperidin-1-yl-[5-(3-piperidin-1-yl-propoxy)-1H-pyrrolo[2, 3-b]pyridin-2-yl]-methanone,

[5-(3-piperidin-1-yl-propoxy)-1H-pyrrolo[2,3-b]-pyridin-2-yl]-pyrrolidin-1-yl-methanone, 5-(3-piperidin-1-yl-propoxy)-1H-pyrrolo[2,3-b]-pyridine-2-carboxylic acid 4-fluoro-benzylamide, morpholin-4-yl-[5-(3-pyrrolidin-1-yl-propoxy)-1H-pyrrolo [2,3-b]pyridin-2-yl]-methanone, piperidin-1-yl-[5-(3-pyrrolidin-1-yl-propoxy)-1H-pyrrolo [2,3-b]pyridin-2-yl]-methanone, pyrrolidin-1-yl-[5-(3-pyrrolidin-1-yl-propoxy)-1H-pyrrolo [2,3-b]pyridin-2-yl]-methanone, 5-(3-pyrrolidin-1-yl-propoxy)-1H-pyrrolo[2,3-b]-pyridine-2-carboxylic acid 4-fluoro-benzylamide, (4,4-difluoro-piperidin-1-yl)-{5-[3-((2R,5R)-2,5-dimethyl-pyrrolidin-1-yl)-propoxy]-1H-pyrrolo[2,3-b]pyridin-2-yl}-methanone, (4,4-difluoro-piperidin-1-yl)-{5-[3-((R)-2-methyl-pyrrolidin-1-yl)-propoxy]-1H-pyrrolo[2,3-b]pyridin-2-yl}-methanone, (4,4-difluoro-piperidin-1-yl)-{5-[3-((S)-2-methyl-pyrrolidin-1-yl)-propoxy]-1H-pyrrolo[2,3-b]pyridin-2-yl}-methanone,

[5-(1-cyclopropyl-piperidin-4-yloxy)-1H-pyrrolo[2,3-b]-pyridin-2-yl]-morpholin-4-yl-methanone, (4,4-difluoro-piperidin-1-yl)-[5-(1-isopropyl-piperidin-4-yloxy)-1H-pyrrolo[2,3-b]pyridin-2-yl]-methanone, 5-(1-isopropyl-piperidin-4-yloxy)-1H-pyrrolo[2,3-b]-pyridine-2-carboxylic acid 4-fluoro-benzylamide,

[5-(1-isopropyl-piperidin-4-yloxy)-1H-pyrrolo[2,3-b]-pyridin-2-yl]-piperidin-1-yl-methanone,

[5-(1-isopropyl-piperidin-4-yloxy)-1H-pyrrolo[2,3-b]-pyridin-1-yl]-morpholin-4-yl-methanone,

[5-(1-isopropyl-piperidin-4-yloxy)-1H-pyrrolo[2,3-b]-pyridin-2-yl]-pyrrolidin-1-yl-methanone, (4,4-difluoro-piperidin-1-yl)-[5-(1-isopropyl-piperidin-4-yloxy)-1-methanesulfonyl-1H-pyrrolo[2,3-b]pyridin-2-yl]-methanone, (4,4-difluoro-piperidin-1-yl)-{1-methanesulfonyl-5-[3-((S)-2-methyl-pyrrolidin-1-yl)-propoxy]-1H-pyrrolo[2,3-b]pyridin-2-yl}-methanone, (4,4-difluoro-piperidin-1-yl)-{1-methanesulfonyl-5-[3-((R)-2-methyl-pyrrolidin-1-yl)-propoxy]-1H-pyrrolo-[2,3-b]pyridin-2-yl}-methanone, (4,4-difluoro-piperidin-1-yl)-[5-(1-isopropyl-piperidin-4-yloxy)-1-(2-methoxy-ethyl)-1H-pyrrolo[2,3-b]pyridin-2-yl]-methanone, (4,4-difluoro-piperidin-1-yl)-[1-isopropyl-5-(1-isopropyl-piperidin-4-yloxy)-1H-pyrrolo[2,3-b]pyridin-2-yl]-methanone,

[1-cyclopropylmethyl-5-(1-isopropyl-piperidin-4-yloxy)-1H-pyrrolo[2,3-b]pyridin-2-yl]-(4,4-difluoro-piperidin-1-yl)-methanone,

[2-(4,4-difluoro-piperidine-1-carbonyl)-5-(1-isopropyl-piperidin-4-yloxy)-pyrrolo[2,3-b]pyridin-1-yl]-acetonitrile, (4,4-difluoro-piperidin-1-yl)-[5-(1-isopropyl-piperidin-4-yloxy)-1-(2,2,2-trifluoro-ethyl)-1H-pyrrolo[2,3-b]pyridin-2-yl]-methanone, (4,4-difluoro-piperidin-1-yl)-[1-(2-hydroxy-ethyl)-5-(1-isopropyl-piperidin-4-yloxy)-1H-pyrrolo[2,3-b]pyridin-2-yl]-methanone, (4,4-difluoro-piperidin-1-yl)-{1-isopropyl-5-[3-((R)-2-methyl-pyrrolidin-1-yl)-propoxy]-1H-pyrrolo[2,3-b]pyridin-2-yl}-methanone, {1-cyclopropylmethyl-5-[3-((R)-2-methyl-pyrrolidin-1-yl)-propoxy]-1H-pyrrolo[2,3-b]pyridin-2-yl}-(4,4-difluoro-piperidin-1-yl)-methanone, {2-(4,4-difluoro-piperidine-1-carbonyl)-5-[3-((R)-2-methyl-pyrrolidin-1-yl)-propoxy]-pyrrolo[2,3-b]pyridin-1-yl}-acetonitrile, (4,4-difluoro-piperidin-1-yl)-[5-[3-((R)-2-methyl-pyrrolidin-1-yl)-propoxy]-1-(2,2,2-trifluoro-ethyl)-1H-pyrrolo[2,3-b]pyridin-2-yl]-methanone, {1-(4-chloro-phenyl)-5-[3-((R)-2-methyl-pyrrolidin-1-yl)-propoxy]-1H-pyrrolo[2,3-b]pyridin-2-yl}-(4,4-difluoro-piperidin-1-yl)-methanone,

[6-chloro-5-(1-isopropyl-piperidin-4-yloxy)-1H-pyrrolo[2,3-b]pyridin-2-yl]-(4,4-difluoro-piperidin-1-yl)-methanone,

[6-chloro-5-(1-isopropyl-piperidin-4-yloxy)-1-(2,2,2-trifluoro-ethyl)-1H-pyrrolo[2,3-b]pyridin-2-yl]-(4,4-difluoro-piperidin-1-yl)-methanone,

[6-chloro-1-cyclopropylmethyl-5-(1-isopropyl-piperidin-4-yloxy)-1H-pyrrolo[2,3-b]pyridin-2-yl]-(4,4-difluoro-piperidin-1-yl)-methanone, and pharmaceutically acceptable salts thereof.

Particularly preferred compounds of formula I of the present invention are the following:

(4,4-difluoro-piperidin-1-yl)-{5-[3-((R)-2-methyl-pyrrolidin-1-yl)-propoxy]-1H-pyrrolo[2,3-b]pyridin-2-yl}-methanone, (4,4-difluoro-piperidin-1-yl)-[5-(1-isopropyl-piperidin-4-yloxy)-1H-pyrrolo[2,3-b]pyridin-2-yl]-methanone, (4,4-difluoro-piperidin-1-yl)-[1-isopropyl-5-(1-isopropyl-piperidin-4-yloxy)-1H-pyrrolo[2,3-b]pyridin-2-yl]-methanone,

[1-cyclopropylmethyl-5-(1-isopropyl-piperidin-4-yloxy)-1H-pyrrolo[2,3-b]pyridin-2-yl]-(4,4-difluoro-piperidin-1-yl)-methanone,

[2-(4,4-difluoro-piperidine-1-carbonyl)-5-(1-isopropyl-piperidin-4-yloxy)-pyrrolo[2,3-b]pyridin-1-yl]-acetonitrile,

[6-chloro-5-(1-isopropyl-piperidin-4-yloxy)-1H-pyrrolo[2,3-b]pyridin-2-yl]-(4,4-difluoro-piperidin-1-yl)-methanone,

[6-chloro-5-(1-isopropyl-piperidin-4-yloxy)-1-(2,2,2-trifluoro-ethyl)-1H-pyrrolo[2,3-b]pyridin-2-yl]-(4,4-difluoro-piperidin-1-yl)-methanone,

[6-chloro-1-cyclopropylmethyl-5-(1-isopropyl-piperidin-4-yloxy)-1H-pyrrolo[2,3-b]pyridin-2-yl]-(4,4-difluoro-piperidin-1-yl)-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, triturate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a compound of the formula II

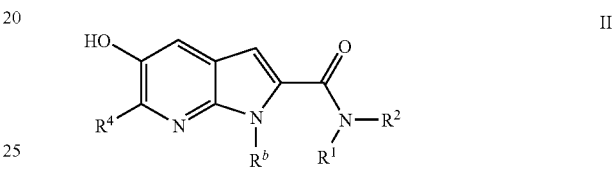

wherein $R^1$, $R^2$ and $R^4$ are as defined herein before and $R^b$ is hydrogen or tert-butoxycarbonyl, with an alcohol of the formula III

HO—$R^5$     III wherein $R^5$ is as defined herein before, in the presence of a trialkylphosphine or triphenylphosphine and of an azo compound to obtain a compound of the formula IA

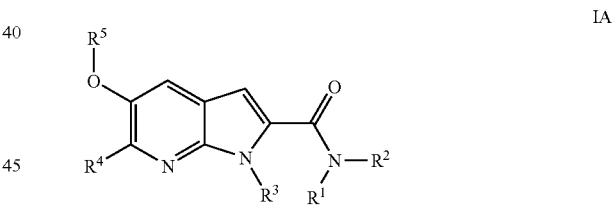

wherein $R^3$ is hydrogen, and optionally transferring into a compound of formula IB

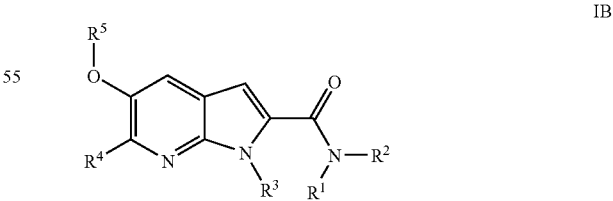

wherein $R^3$ is a group as defined herein before other than hydrogen, and if desired, converting the compound obtained into a pharmaceutically acceptable acid addition salt, or alternatively, b) coupling a compound of formula IV

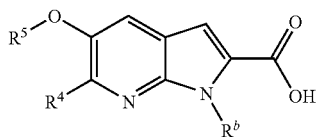

wherein $R^4$ and $R^5$ are as defined herein before and $R^b$ is hydrogen or tert-butoxycarbonyl, with an amine of the formula V

wherein $R^1$ and $R^2$ are as defined herein before, under basic conditions to obtain a compound of the formula IA

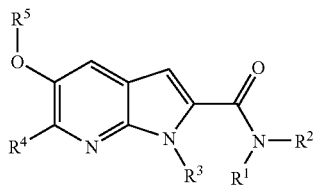

wherein $R^3$ is hydrogen, and optionally transferring into a compound of formula IB

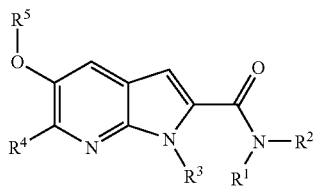

wherein $R^3$ is a group as defined herein before other than hydrogen, and if desired, converting the compound obtained into a pharmaceutically acceptable acid addition salt.

Transferring into a compound of formula IB means treating the compound of formula IA with a suitable base in a suitable solvent under anhydrous conditions (e.g. sodium hydride in DMF) and reacting the intermediate anion with an alkylating or acylating agent $R^3$—X wherein X signifies a leaving group such as e.g. iodide, bromide, methanesulfonate or chloride, to obtain a compound of formula IB wherein $R^3$ signifies lower alkyl, lower hydroxyalkyl, lower alkoxyalkyl, lower halogenalkyl, lower cycloalkylalkyl, lower alkanoyl, lower cyanoalkyl, lower alkylsulfonyl or phenylsulfonyl, or alternatively, transferring into a compound of formula IB means reacting a compound of formula IA with an optionally substituted phenylboronic acid using an appropriate catalyst (e.g. copper (IT) acetate) and base (e.g. pyridine) in a suitable solvent like, e.g. dichloromethane, to obtain a compounds of formula IB where $R^3$ signifies a phenyl or a substituted phenyl group.

Typical examples of an alkylating or acylating agent $R^3$—X are methyl iodide, 2-bromopropane, 2,2,2-trifluoro-ethyl-methanesulfonate, methanesulfonylchloride or phenylsulfonylchloride.

The preparation of compounds of formula I of the present invention may be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the description or in the examples, or by methods known in the art.

Scheme 1

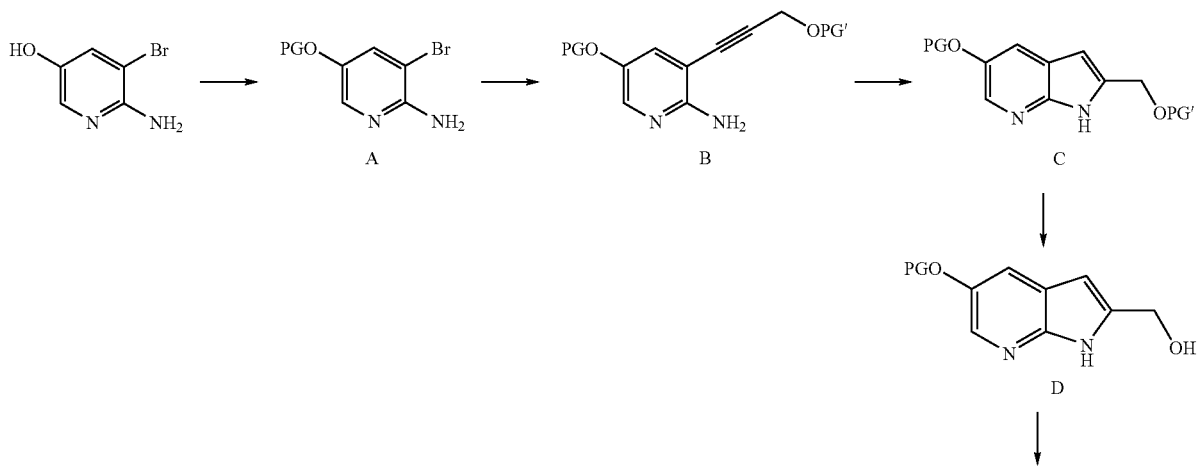

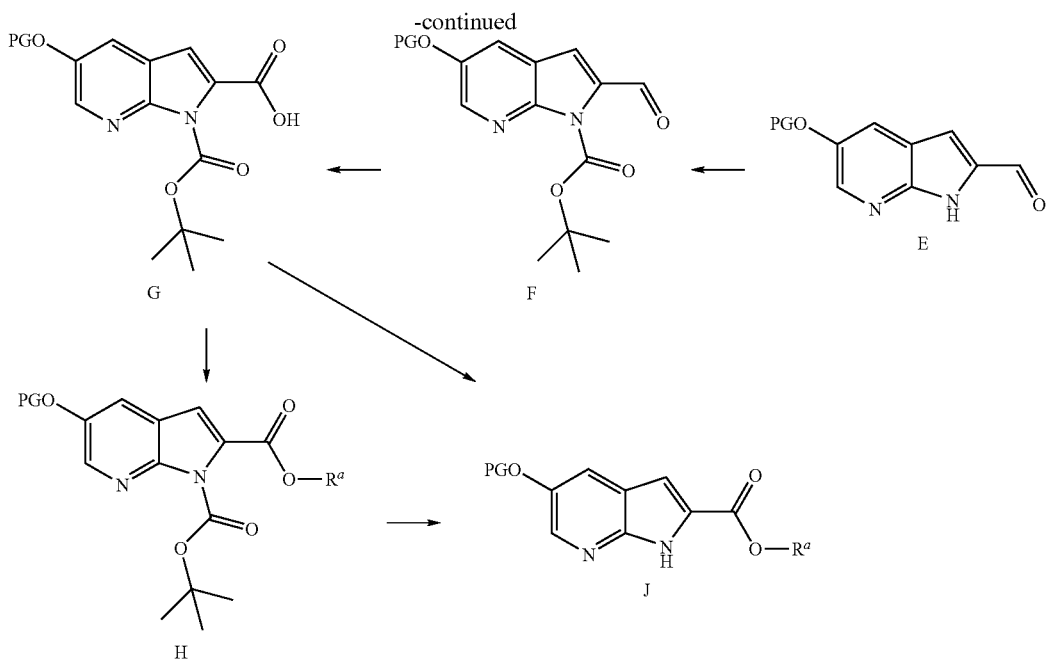

7-Aza-indole-2-carboxylates of formula J can be prepared as depicted in scheme 1 starting from 6-amino-5-bromo-pyridin-3-ol (as prepared according to WO98/25920), which can be O-protected with, e.g. a benzyl protective group by using, e.g. benzyl bromide and a base such as, e.g. sodium hydride in an appropriate solvent such as, e.g. DMF. PG thus means a hydroxy protecting group, e.g. a benzyl group. Reaction of intermediate A with optionally protected (e.g. with a dimethylthexylsilyl protective group) carbinol derivatives leads to intermediate B. PG' thus means a hydroxy protecting group, e.g. a silyl protecting group such as dimethylthexylsilyl. The reaction proceeds in the presence of a suitable catalyst (e.g. bis-triphenylphosphine palladium dichloride and copper(I) iodide as co-catalyst) in a suitable solvent (e.g. triethylamine). The intermediate B is treated with an acid anhydride such as, e.g. trifluoroacetic anhydride and the resulting trifluoroacetamide is cyclized to the 7-aza-indole intermediate C by treatment with a suitable catalyst (e.g. bis-triphenylphosphine palladium dichloride and copper(I) iodide as co-catalyst) in a suitable solvent such as, e.g. N,N-diisopropylethylamine. Removal of the silyl protective group with, e.g. tetra-n-butylammonium fluoride in a suitable solvent such as, e.g. THF yields intermediate D which after oxidation of the alcohol with, e.g. manganese dioxide in, e.g. dichloromethane gives intermediate E, Boc-protection of the indole nitrogen using, e.g. di-tert-butyl dicarbonate in, e.g. dichloromethane yields intermediate F. Oxidation of the aldehyde functionality according to methods known to those skilled in the art and described in literature (e.g. Amos B. Smith 111 et. al, J. Am. Chem. Soc. 1989, 111 (15), 5761-5768) yields intermediate G. Treatment of intermediate G with sulfuric acid hi methanol furnishes intermediate J. In this case, $R^a$ signifies a methyl group. Intermediate J can also be obtained through removal of the Boc protective group from intermediate H under acidic conditions (e.g. with trifluoroacetic acid in, e.g. dichloromethane). Intermediate H in turn can be synthesized from intermediate G through treatment with a suitable base in a suitable solvent under anhydrous conditions (e.g. sodium hydride in DMF) and reaction of the intermediate anion with an alkylating agent $R^a$—X such as, e.g. methyl iodide. $R^a$ in scheme 1 is an alkyl group, preferably a lower alkyl group, preferably methyl or ethyl. X signifies a leaving group such as, e.g. chlorine, bromine or trifluoromethanesulfonate.

Scheme 2

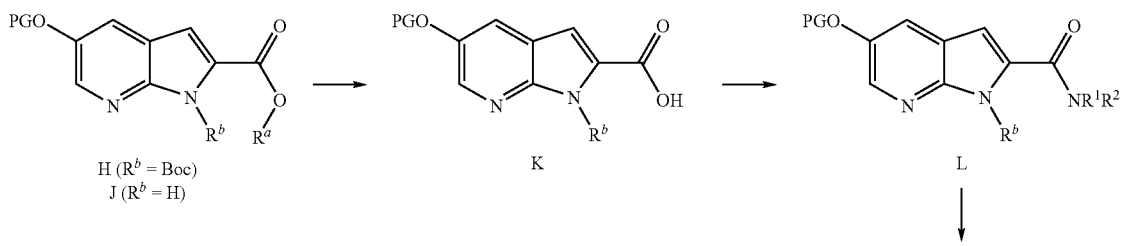

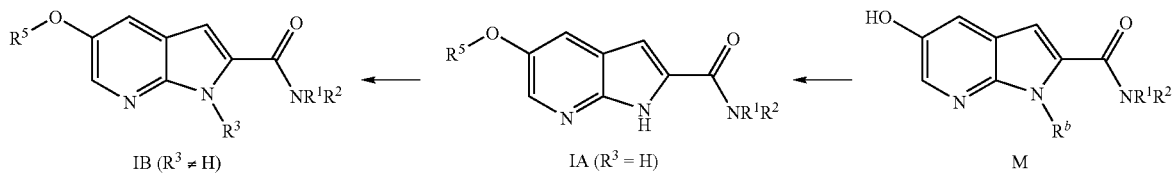

Compounds of the general formula IA and IB can be prepared according to scheme 2. The ester functionality in intermediates H or J is cleaved under basic (e.g. with lithium hydroxide in polar solvents such as, e.g. methanol, water or THF or mixtures of said solvents) or under acidic conditions (e.g. using concentrated hydrochloric acid in THF) and the resulting either lithium or hydrochloride salts of intermediate K are further reacted with amines to furnish the amide intermediates L. The coupling of carboxylic acids with amines (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. dimethylformamide (DMF) or dioxane in the presence of a base (e.g. triethylamine or diisopropylethylamine). The protective group PG is cleaved off by methods known by those skilled in the art and as described in literature (e.g. T. W. Greene and P. G. M. Wuts. Protective Groups in Organic Synthesis. 3$^{rd}$ Edition, 1999) to give intermediate M. For example, a benzyl protective group is cleaved off by, e.g. hydrogenolysis using an appropriate catalyst (e.g. palladium on charcoal) in a suitable solvent or solvent mixture (e.g. ethyl acetate, methanol). Compounds of the general formula IA can be prepared as follows: In case of Het I or Het II, the resulting phenol is coupled with alcohols of the type HO-Het I or HO-Het II (either commercially available or accessible by methods described in references or by methods known in the art) applying the so-called "Mitsunobu reaction" which is known to those skilled in the art and widely described (e.g. D. L. Hughes. The Mitsunobu reaction. Organic Reactions (New York) (1992), 42, 335-656). Thereby the phenol intermediate is coupled with alcohols of the type HO-Het I or HO-Het II using a phosphine like, e.g. tributylphosphine or triphenylphosphine and either a azodicarboxylic acid dialkyl ester like, e.g. diethyl azodicarboxylate (DEAD) or diisopropylazodicarboxylate (DIAD) or using N,N,N',N'-tetramethylazodicarboxamide in a solvent commonly used in such transformations like, e.g. tetrahydrofuran (THF), toluene or dichloromethane. In cases where the substituents $R^6$ or $R^7$ are not already present in the alcohols of the type HO-Het I or HO-Het II, they can be introduced by alkylation of the free amine functionality in compounds of formula IA or IB by employing methods described in references or by methods known in the art such as, e.g. reductive amination (e.g. F. Zaragoza, et. al, J. Med. Chem. 2004, 47, 2833-2838). To this extent, compounds of formula IA might be protected first with a suitable protective group such as, e.g. a tert-butoxycarbonyl group, which after introduction of $R^6$ or $R^7$ can be removed under conditions known those skilled in the art and as described under scheme 1. The before mentioned methodology can be also applied for alcohols of type HO-Het III, or, alternatively, the phenol intermediate is alkylated with α,ω-dihalo-alkanes such as, e.g. 1-bromo-3-chloropropane under basic conditions (e.g. potassium carbonate) in a suitable solvent (e.g. 2-butanone) and reacting the intermediate chloropropoxy compound with an amine in the presence of a base such as, e.g. potassium carbonate in an appropriate solvent such as, e.g. acetonitrile. In case where $R^b$ signifies a protective group such as, e.g. a tert-butoxycarbonyl protective group, the protective group is cleaved off by methods known by those skilled in the art and as described in literature (e.g. T. W. Greene and P. G. M. Wuts. Protective Groups in Organic Synthesis. 3$^{rd}$ Edition, 1999) to give the compounds of the general formula IA. Intermediates of formula I B can be obtained for example through treatment of intermediates of formula IA with a suitable base in a suitable solvent under anhydrous conditions (e.g. sodium hydride in DMF) and reaction the intermediate anion with an alkylating or acylating agent $R^3$—X such as, e.g. methyl iodide, 2-bromopropane, 2,2,2-trifluoroethyl-methanesulfonate, methanesulfonyl- or phenylsulfonylchloride. In those cases $R^3$ signifies a methyl, trifluoromethyl, isopropyl or an alkyl- or arylsulfonyl group and X signifies a leaving group such as, e.g. iodide, bromide, methanesulfonate or chloride. Compounds of formula IB where $R^3$ signifies a phenyl or a substituted phenyl group can be synthesized by processes known to those skilled in the art and described in literature (e.g. W. W. K. R. Mederski et. al, Tetrahedron, 1999, 55, 12757). For example, intermediates of formula IA are reacted with an optionally substituted phenylboronic acid using an appropriate catalyst (e.g. copper(II) acetate) and base (e.g. pyridine) in a suitable solvent like, e.g. dichloromethane. $R^a$ in scheme 2 is an alkyl group, preferably a lower alkyl group, preferably methyl or ethyl. $R^b$ signifies hydrogen or a protective group such as, e.g. tert-butoxycarbonyl. PG signifies a protective group such as, e.g. a benzyl protective group.

$R^a$ in scheme 2 is an alkyl group, preferably a lower alkyl group, preferably methyl or ethyl. $R^b$ signifies hydrogen or a protective group such as, e.g. tert-butoxycarbonyl. PG signifies a protective group such as, e.g. a benzyl protective group.

Scheme 3

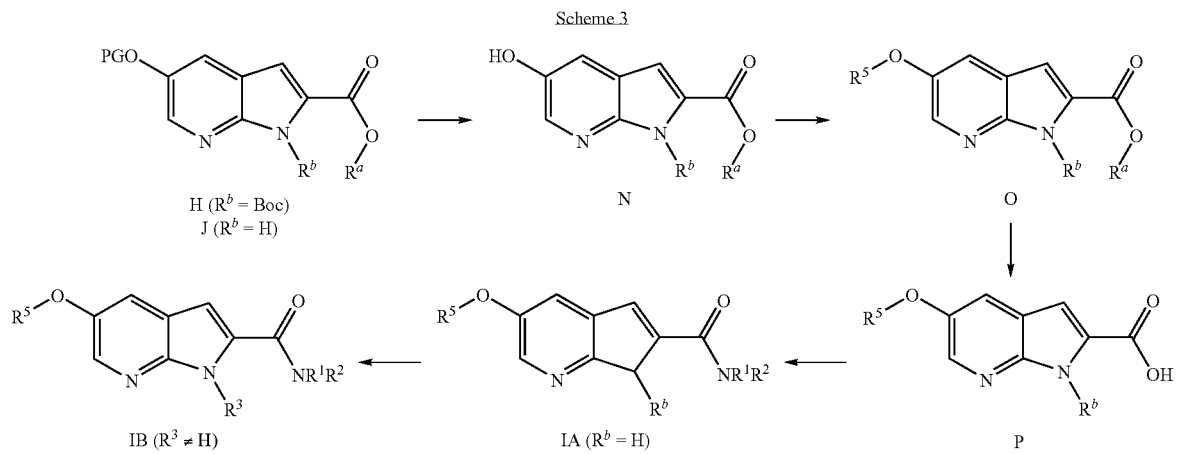

Compounds of the general formula IA and IB can be also prepared according to scheme 3 applying the methods described and mentioned for scheme 2. $R^a$ in scheme 3 is an alkyl group, preferably a lower alkyl group, preferably methyl or ethyl. $R^b$ signifies hydrogen or a protective group such as, e.g. a tert-butoxycarbonyl group. PG signifies a protective group such as, e.g. a benzyl protective group.

conditions, such as e.g. meta-chloroperbenzoic acid in dichloromethane. The resulting intermediate Q is then treated with a nucleophilic system, such as, e.g. ethyl chloroformate or benzoic acid bromide in the presence of a suitable base like, e.g. hexamethyldisilazane in a suitable solvent such as, e.g. tetrahydrofuran to furnish intermediate R. Intermediate R in turn can be further transformed via intermediates S and T into Scheme 4

Compounds of general formula I in which $R^4$ signifies a chlorine or bromine atom can be prepared according to scheme 4. Optionally N,O protected (e.g. with a tert-butoxycarbonyl protective group at the indole nitrogen (PG″) and a benzyl protective group at the oxygen in position 5 (PG)) 7-aza-indole-2-carboxylates of formula H are oxidized at the pyridine nitrogen to the N-oxide under appropriate oxidizing compounds of the general formula IC or ID by methods outlined before. $R^a$ in scheme 4 is an alkyl group, preferably a lower alkyl group, preferably methyl or ethyl. PG and PG″ signify a protective group, such as, e.g. a benzyl protective group for PG and, e.g. a tert-butoxycarbonyl protective group as PG″.

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome x, and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of II3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a medicament for the treatment and prevention of obesity in a patient who is also receiving treatment with a a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an object of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an object of the present invention.

It is a further preferred object to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like: 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (syincor) and the like; 7) Tyrosine Hydroxylase Inhibitors, including metyrosine (demser), and the like; 8) Neutral Endopeptidase Inhibitors, including BMS 186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165, and the like.

Also an object of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an object of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard topcounter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. (Compounds that showed an inhibition of [$^3$H]-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit K, values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 5 | 25.5 |
| Example 13 | 28.9 |
| Example 22 | 9.4 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Example 1

Morpholin-4-yl-[5-(3-piperidin-1-yl-propoxy)-1H-pyrrolo[2,3-b]pyridin-2-yl]-methanone To the suspension of 45 mg (0.13 mmol) 5-(3-piperidin-1-yl-propoxy)-lII-pyrrolo[2,3-b]pyridine-2-carboxylic acid hydrochloride in 0.6 ml DMF, 53 mg (0.16 mmol) O-(benzotriazol-1-yl)-N,N,N',N'-tetramethyluronium tetrafluoroborate, 14 ml (14 mg; 0.16 mmol) morpholine and 0.16 ml (0.12 g, 0.93 mmol) N,N-diisopropyl-ethylamine were added. After 75 min. the reaction mixture was poured on saturated aqueous sodium bicarbonate solution and was extracted three times with dichloromethane. The combined organic layers were washed with brine, dried over magnesium sulfate, filtered and evaporated. The residue was flash-chromatographed on silica gel with dichloromethane:methanol:ammonia (9:1:0.1 v/v) as eluant to give 42 mg (85%) of the desired compound as a light brown solid.

MS (ISP): 373.2 (M+H$^+$)

Intermediates a) 5-(3-Chloro-propoxy)-1H-pyrrolo[2,3-b]pyridine-2-carboxylic Acid Ethyl Ester The suspension consistent of 0.5 g (2.4 mmol) 5-hydroxy-pyrrolo[2,3-b]pyridine-1,2-dicarboxylic acid 1-tert-butyl ester 2-ethyl ester (as prepared in WO 05/000849), 0.4 g (2.6 mmol) potassium carbonate and 0.29 ml (0.46 g, 2.9 mmol) 1-bromo-3-chloropropane in 10 ml 2-butanone was heated under reflux for 23 hours. The reaction mixture was poured on 10% aqueous ammonium chloride solution and was extracted three times with ethyl acetate. The combined organic layers were washed with brine, dried over magnesium sulfate, filtered and evaporated. The residue was flash-chromatographed on silica gel with n-heptane:ethyl acetate (1:1 v/v) as eluant to give 0.22 g (32%) of the desired compound as a colorless solid.

MS (EI): 282.1 (M)

b) 5-(3-Piperidin-1-yl-propoxy)-1H-pyrrolo[2,3-b]pyridine-2-carboxylic Acid Ethyl Ester The suspension consistent of 0.20 g (0.71 mmol) 5-(3-chloro-propoxy)-1H-pyrrolo[2,3-b]pyridine-2-carboxylic acid ethyl ester, 0.12 g (0.85 mmol) potassium carbonate, 0.12 g (0.71 mmol) potassium iodide and 84 ml (72 µg, 0.85 mmol) piperidine was heated under reflux for 17 hours. After cooling down to room temperature the reaction mixture was poured on water and was extracted three times with ethyl acetate. The combined organic layers were washed with brine, dried over magnesium sulfate, filtered and evaporated. The residue was flash-chromatographed on silica gel with dichloromethane:methanol:ammonia (9:1:0.1 v/v) as eluant to give 0.16 g (68%) of the desired compound as a light yellow solid.

MS (ISP): 332.4 (M+H$^+$)

c) 5-(3-Piperidin-1-yl-propoxy)-1H-pyrrolo[2,3-b]pyridine-2-carboxylic Acid Hydrochloride To the solution of 0.18 g (0.54 mmol) 5-(3-piperidin-1-yl-propoxy)-1H-pyrrolo[2,3-b]pyridine-2-carboxylic acid ethyl ester in 1.2 ml dioxan, 0.54 ml (0.64 g) concentrated hydrochloric acid were added. The reaction mixture was heated under reflux for 18 h, evaporated and dried under high vacuum over phosphorus pentoxide to give 0.18 g (100%) of the compound as a light brown solid.

MS (ISP): 304.4 (M+H$^+$)

Example 2

Piperidin-1-yl-[5-(3-piperidin-1-yl-propoxy)-1H-pyrrolo[2,3-b]pyridin-2-yl]-methanone The title compound was synthesized in analogy to example 1 from 5-(3-piperidin-1-yl-propoxy)-1H-pyrrolo[2,3-b]pyridine-2-carboxylic acid hydrochloride and piperidine to give the desired product as a light brown solid (75%).

MS (TIC): 371.1 (M+H$^+$)

Example 3

[5-(3-Piperidin-1-yl-propoxy)-1H-pyrrolo[2,3-b]pyridin-2-yl]-pyrrolidin-1-yl-methanone The title compound was synthesized in analogy to example 1 from 5-(3-piperidin-1-yl-propoxy)-1H-pyrrolo[2,3-b]pyridine-2-carboxylic acid hydrochloride and pyrrolidine to give the desired product as a colorless solid (70%).

MS (TIC): 357.1 (M+H$^+$)

Example 4

5-(3-Piperidin-1-yl-propoxy)-1H-pyrrolo[2,3-b]pyridine-2-carboxylic Acid 4-fluoro-benzylamide The title compound was synthesized in analogy to example 1 from 5-(3-piperidin-1-yl-propoxy)-1H-pyrrolo[2,3-b]pyridine-2-carboxylic acid hydrochloride and 4-fluorobenzylamine to give the desired product as light brown solid (55%).

MS (ISP): 411.2. (M+H$^+$)

Example 5

Morpholin-4-yl-[5-(3-pyrrolidin-1-yl-propoxy)-1H-pyrrolo[2,3-b]pyridin-2-yl]-methanone The title compound was synthesized in analogy to example 1 from lithium 5-(3-pyrrolidin-1-yl-propoxy)-1H-pyrrolo[2,3-b]pyridine-2-carboxylate, O-(benzotriazol-1-yl)-N,N,N', N'-tetramethyluronium tetrafluoroborate, morpholine and N,N-diisopropylethylamine to give the desired product as a light yellow solid (55%).

MS (TIC): 359.1 (M+H$^+$)

Intermediates a) 5-(3-Pyrrolidin-1-yl-propoxy)-1H-pyrrolo[2,3-b]pyridine-2-carboxylic Acid Ethyl Ester The title compound was synthesized in analogy to example 1, intermediate b), from 5-(3-chloro-propoxy)-1H-pyrrolo[2,3-b]pyridine-2-carboxylic acid ethyl ester, potassium carbonate, potassium iodide and pyrrolidine to give the desired product as light yellow solid (75%).

MS (TIC): 318.0 (M+H$^+$)

b) Lithium 5-(3-pyrrolidin-1-yl-propoxy)-1H-pyrrolo[2,3-b]pyridine-2-carboxylate To the suspension of 0.19 g (0.6 mmol) 5-(3-pyrrolidin-1-yl-propoxy)-1H-pyrrolo[2,3-b]pyridine-2-carboxylic acid ethyl ester in 0.4 ml water, 0.4 ml methanol and 0.4 ml tetrahydrofuran was cooled to 0° C. and treated with 0.63 ml (0.63 mmol) of a 1M aqueous lithium hydroxide solution. After stirring for 5 hours at room temperature the volatile components were evaporated at a rotary evaporator and the residue dried under high vacuum over phosphorus pentoxide to give 0.18 g (100%) of the compound as a light yellow solid (100%).

MS (TIC): 288.1 (M−H$^+$)

Example 6

Piperidin-1-yl-[5-(3-pyrrolidin-1-yl-propoxy)-1H-pyrrolo[2,3-b]pyridin-2-yl]-methanone The title compound was synthesized in analogy to example 1 from lithium 5-(3-pyrrolidin-1-yl-propoxy)-1H-pyrrolo[2,3-b]pyridine-2-carboxylate, O-(benzotriazol-1-yl)-N,N,N',N'-tetramethyluronium tetrafluoroborate, piperidine and N,N-diisopropylethylamine to give the desired product as a light brown solid (32% G).

MS (TIC): 357.2 (M+H$^+$)

Example 7

Pyrrolidin-1-yl-[5-(3-pyrrolidin-1-yl-propoxy)-1H-pyrrolo[2,3-b]pyridin-2-yl]-methanone The title compound was synthesized in analogy to example 1 from lithium 5-(3-pyrrolidin-1-yl-propoxy)-1H-pyrrolo[2,3-b]pyridine-2-carboxylate, O-(benzotriazol-1-yl)-N,N,N',N'-tetramethyluronium tetrafluoroborate, pyrrolidine and N,N-diisopropylethylamine to give the desired product as a light yellow solid (53%).

MS (TIC): 343.0 (M+H$^+$)

Example 8

5-(3-Pyrrolidin-1-yl-propoxy)-1H-pyrrolo[2,3-b]pyridine-2-carboxylic Acid 4-fluoro-benzylamide The title compound was synthesized in analogy to example 1 from lithium 5-(3-pyrrolidin-1-yl-propoxy)-1H-pyrrolo[2,3-b]pyridine-2-carboxylate, O-(benzotriazol-1-yl)-N,N,N',N'-tetramethyluronium tetrafluoroborate, 4-fluorobenzylamine and N,N-diisopropylethylamine to give the desired product as a light yellow solid (29%).

MS (TIC): 397.0 (M+H$^+$)

Example 9

(4,4-Difluoro-piperidin-1-yl)-[5-[3-((2R,5R)-2,5-dimethyl-pyrrolidin-1-yl)-propoxy]-1H-pyrrolo[2,3-b]pyridin-2-yl]-methanone The title compound was synthesized in analogy to example 1, intermediate a), from [5-(3-chloro-propoxy)-1H-pyrrolo[2,3-b]pyridin-2-yl]-(4,4-difluoro-piperidin-1-yl)-methanone, (2R,5R)-(−)-trans-2,5-dimethylpyrrolidine (commercially available) and potassium carbonate in acetonitrile to give 23 mg (6%) of the desired product as a light yellow solid.

MS (TIC): 421.1 (M+H$^+$)

Intermediates a) 5-Benzyloxy-2-(4,4-difluoro-piperidine-1-carbonyl)-pyrrolo[2,3-b]pyridine-1-carboxylic Acid tert-butyl Ester To the solution of 2.3 g (6.2 mmol) 5-benzyloxy-pyrrolo[2,3-b]pyridine-1,2-dicarboxylic acid 1-tert-butyl ester (intermediate G), 2.5 g (7.8 mmol) O-(benzotriazol-1-yl)-N,N,N',N'-tetramethyluronium tetrafluoroborate and 1.2 g (7.8 mmol) 4,4-difluoropiperidine hydrochloride in 30 ml DMF, 6.4 ml (4.8 g, 37.4 mmol) N,N-diisopropylethylamine were added. After 40 min. stirring at room temperature the clear solution was poured on saturated aqueous sodium bicarbonate solution and was extracted three times with ethyl acetate. The combined organic layers were washed three times with water and with brine, dried over magnesium sulfate, filtered and evaporated. The residue was re-crystallized from dichloromethane and n-heptane to give 2.8 g (95%) of the desired compound as a colorless solid.

MS (TIC): 472.0 (M+H$^+$)

b) 2-(4,4-Difluoro-piperidine-1-carbonyl)-5-hydroxy-pyrrolo[2,3-b]pyridine-1-carboxylic Acid tert-butyl Ester To the solution of 0.3 g (0.64 mmol) 5-benzyloxy-2-(4,4-difluoro-piperidine-1-carbonyl)-pyrrolo[2,3-b]pyridine-1-carboxylic acid tert-butyl ester in 3 ml methanol and 4 ml ethyl acetate 45 mg palladium on activated charcoal (10%) was added and the suspension was hydrogenated at 1.3 bar for 15 min. The suspension was filtered over Dicalite Speed Plus®(Aldrich), the filtercake was washed with ethyl acetate and methanol and the filtrate evaporated. The residue was purified by flash column chromatography on silica gel with ethyl acetate:n-heptane (2:1) as eluant to give 0.19 g (78%) of the desired compound as a colorless solid.

MS (TIC): 382.0 (M+H$^+$)

c) 5-(3-Chloro-propoxy)-2-(4,4-difluoro-piperidine-1-carbonyl)-pyrrolo[2,3-b]pyridine-1-carboxylic Acid tert-butyl Ester The title compound was synthesized in analogy to example 1, intermediate a), from 2-(4,4-difluoro-piperidine-1-carbonyl)-5-hydroxy-pyrrolo[2,3-b]pyridine-1-carboxylic acid tert-butyl ester, potassium carbonate and 1-bromo-3-chloropropane in 2-butanone to give the desired product as a colorless foam (63%).

MS (TIC): 458.2 (M+H$^+$)

d) [5-(3-Chloro-propoxy)-1H-pyrrolo[2,3-b]pyridin-2-yl]-(4,4-difluoro-piperidin-1-yl)-methanone The solution of 1.3 g (2.8 mmol) 5-(3-chloro-propoxy)-2-(4,4-difluoro-piperidine-1-carbonyl)-pyrrolo[2,3-b]pyridine-1-carboxylic acid tert-butyl ester in 15 ml dichloromethane was cooled down to 0° C., then 4.2 ml (6.3 g, 55.5 mmol) trifluoroacetic acid was added and the cooling bath was removed. After 1.5 hours the solution was cooled again down to 0° C. and 60 ml of an aqueous 1M sodium hydroxide solution was added slowly. The solution was extracted three times with dichloromethane, the combined organic layers were washed with brine, dried over magnesium sulfate, filtered and 50 ml n-heptane) was added. The dichloromethane was evaporated at a rotary evaporator and the resulting suspension was filtered and washed with n-heptane and the colorless solid (0.92 g, 93%) was dried under high vacuum.

MS (TIC): 358.0 (M+H$^+$)

Example 10

(4,4-Difluoro-piperidin-1-yl)-{5-[3-((R)-2-methyl-pyrrolidin-1-yl)-propoxy]-1H-pyrrolo[2,3-b]pyridin-2-yl}-methanone The title compound was synthesized in analogy to example 1, intermediate a), from [5-(3-chloro-propoxy)-1H-pyrrolo[2,3-b]pyridin-2-yl]-(4,4-difluoro-piperidin-1-yl)-methanone, (R)-2-methyl-pyrrolidine hydrochloride (commercially available) and potassium carbonate in acetonitrile to give the desired product as a light brown solid (53%).

MS (TIC): 407.2 (M+H$^+$)

Example 11

(4,4-Difluoro-piperidin-1-yl)-[5-[3-((S)-2-methyl-pyrrolidin-1-yl)-propoxy]-1H-pyrrolo[2,3-b]pyridin-2-yl]-methanone The title compound was synthesized in analogy to example 1, intermediate a), from [5-(3-chloro-propoxy)-1H-pyrrolo[2,3-b]pyridin-2-yl]-(4,4-difluoro-piperidin-1-yl)-methanone, (S)-2-methyl-pyrrolidine hydrochloride (commercially available) and potassium carbonate in acetonitrile to give the desired product as a colorless solid (57%).

MS (TIC): 407.2 (M+H$^+$)

Example 12

[5-(1-Cyclopropyl-piperidin-4-yloxy)-1H-pyrrolo[2,3-b]pyridin-2-yl]-morpholin-4-yl-methanone The solution of 0.16 g (0.34 mmol) 5-(1-cyclopropyl-piperidin-4-yloxy)-2-(morpholine-4-carbonyl)-pyrrolo[2,3-b]pyridine-1-carboxylic acid tert-butyl ester in 2 ml dichloromethane was cooled down to 0° C. and treated with 0.52 ml (0.8 g, 6.8 mmol) trifluoroacetic acid. The cooling bath was removed and after 1 hour at room temperature the solution was evaporated and the residue was flash-chromatographed on silica gel with dichloromethane:methanol:ammonia (9:1:0.1 v/v) as eluant to give 0.1 g (83%) of the desired compound as a colorless solid.

MS (ISP): 371.4 (M+H$^+$)

Intermediates a) 5-Benzyloxy-2-(morpholine-4-carbonyl)-pyrrolo[2,3-b]pyridine-1-carboxylic Acid tert-butyl Ester The title compound was synthesized in analogy to example 9, intermediate a), from 5-benzyloxy-pyrrolo[2,3-b]pyridine-1,2-dicarboxylic acid 1-tert-butyl ester (intermediate G), O-(benzotriazol-1-yl)-N,N,N',N'-tetramethyluronium tetrafluoroborate, morpholine and N,N-diisopropylethylamine in DMF to give the desired product as colorless foam (70%).

MS (TIC): 438.1 (M+H$^+$)

b) 5-Hydroxy-2-(morpholine-4-carbonyl)-pyrrolo[2,3-b]pyridine-1-carboxylic Acid tert-butyl Ester The title compound was synthesized in analogy to example 9, intermediate b), through hydrogenation of 5-benzyloxy-2-(morpholine-4-carbonyl)-pyrrolo[2,3-b]pyridine-1-carboxylic acid tert-butyl ester to give the desired product as a colorless foam (91%).

MS (TIC): 247.8. (M+H$^+$)

c) 5-(1-Cyclopropyl-piperidin-4-yloxy)-2-(morpholine-4-carbonyl)-pyrrolo[2,3-b]pyridine-1-carboxylic Acid tert-butyl Ester To the solution of 73 mg (0.5 mmol) N-cyclopropyl-4-piperidinol in 2 ml tetrahydrofuran, 0.15 g (0.43 mmol) 5-hydroxy-2-(morpholine-4-carbonyl)-pyrrolo[2,3-b]pyridine-1-carboxylic acid tert-butyl ester and 0.14 g (0.52 mmol) triphenylphosphine were added and the suspension cooled to 0° C. Then, 0.12 g (0.52 mmol) diisopropyl azodicarboxylate was added and the resulting solution stirred for 20 hours at room temperature. The solvent was evaporated and the residue flash-chromatographed on silica gel with ethyl acetate: methanol (9:1 v/v) as eluant to give 0.16 g (81%) the product as a colorless gum.

MS (ISP): 471.4 (M+H$^+$)

Example 13

(4,4-Difluoro-piperidin-1-yl)-[5-(1-isopropyl-piperidin-4-yloxy)-1H-pyrrolo[2,3-b]pyridin-2-yl]-methanone The title compound was synthesized in analogy to example 9, intermediate a), from 5-(1-isopropyl-piperidin-4-yloxy)-1H-pyrrolo[2,3-b]pyridine-2-α-carboxylic acid hydrochloride, O-(benzotriazol-1-yl)-N,N,N',N'-tetramethyluronium tetrafluoroborate, 4,4-difluoropiperidine hydrochloride and N,N-diisopropylethylamine (5 eq.) in DMF to give the desired product as an off-white solid (44%).

MS (TIC): 407.2 (M+H$^+$)

Intermediates a) 5-(1-Isopropyl-piperidin-4-yloxy)-pyrrolo[2,3-b]pyridine-1,2-dicarboxylic Acid 1-tert-butyl Ester 2-ethyl Ester To the turbid solution of 0.2 g (0.65 mmol) 5-hydroxy-pyrrolo[2,3-b]pyridine-1,2-dicarboxylic acid 1-tert-butyl ester 2-ethyl ester (as prepared in WO 05/000849) and 1-isopropyl-piperidin-4-ol (commercially available) in 6 ml tetrahydrofuran, 0.26 g (1.3 mmol) tributylphosphine were added and the mixture was cooled to 0° C. Within 60 min.

32.9 mg (1.3 mmol) 1,1'-(azodicarbonyl)dipiperidine were added under stirring and the reaction was allowed to reach room temperature. After 19 hours the brown suspension was filtered and evaporated. The residue was stirred in tert butyl methyl ether, filtered and the clear filtrate was evaporated and flash-chromatographed on silica gel with dichloromethane: methanol:ammonia (9:1:0.1 v/v) to give 60 mg (21%) of the product as a yellow oil.

MS (TIC): 432.2 (M+H$^+$)

b) 5-(1-Isopropyl-piperidin-4-yloxy)-1H-pyrrolo[2, 3-b]pyridine-2-carboxylic Acid Hydrochloride The solution of 0.24 g (0.56 mmol) 5-(1-isopropyl-piperidin-4-yloxy)-pyrrolo[2,3-b]pyridine-1,2-dicarboxylic acid 1-tert-butyl ester 2-ethyl ester in 1.2 ml dioxan is treated with 0.56 ml concentrated hydrochloric acid and stirred for 16 hours under reflux. The volatile components were removed at a rotary evaporator and the residue was dried under high vacuum to give 0.19 g (98%) of the product as a brown foam which was pure enough for the next step without further purification.

MS (TIC): 302.2 (M–H)

Example 14

5-(1-Isopropyl-piperidin-4-yloxy)-1H-pyrrolo[2,3-b] pyridine-2-carboxylic Acid 4-fluoro-benzylamide The title compound was synthesized in analogy to example 9, intermediate a), from 5-(1-isopropyl-piperidin-4-yloxy)-1H-pyrrolo[2,3-b]pyridine-2-carboxylic acid hydrochloride, O-(benzotriazol-1-yl)-N,N,N',N'-tetramethyluronium tetrafluoroborate, 4-fluorobenzylamine and N,N-diisopropylethylamine (7 eq.) in DMF to give the desired product as a light yellow solid (37%).

MS (TIC): 411.2 (M+H$^+$)

Example 15

[5-(1-Isopropyl-piperidin-4-yloxy)-1H-pyrrolo[2,3-b]pyridin-2-yl]-piperidin-1-yl-methanone The title compound was synthesized in analogy to example 9, intermediate a), from 5-(1-isopropyl-piperidin-4-yloxy)-1H-pyrrolo[2,3-b]pyridine-2-carboxylic acid hydrochloride, O-(benzotriazol-1-yl)-N,N,N',N'-tetramethyluronium tetrafluoroborate, piperidine and N,N-diisopropylethylamine (7 eq.) in DMF to give the desired product as a light brown foam (51%).

MS (TIC): 371.1 (M+H$^+$)

Example 16

[5-(1-Isopropyl-piperidin-4-yloxy)-1H-pyrrolo[2,3-b]pyridin-2-yl]-morpholin-4-yl-methanone The title compound was synthesized in analogy to example 9, intermediate a), from (1-isopropyl-piperidin-4-yloxy)-1H-pyrrolo[2,3-b]pyridine-2-carboxylic acid hydrochloride (example 13, intermediate b)), O-(benzotriazol-1-yl)-N,N,N',N'-tetramethyluronium tetrafluoroborate, morpholine and N,N-diisopropylethylamine (7 eq.) in DMF to give the desired product as a yellow solid (70%).

MS (TIC): 373.2 (M+H$^+$)

Example 17

[5-(1-Isopropyl-piperidin-4-yloxy)-1H-pyrrolo[2,3-b]pyridin-2-yl]-pyrrolidin-1-yl-methanone The title compound was synthesized in analogy to example 9, intermediate a), from lithium 1-tert-butoxycarbonyl-5-(1-isopropyl-piperidin-4-yloxy)-1H-pyrrolo[2,3-b]pyridine-2-carboxylate, O-(benzotriazol-1-yl)-N,N,N',N'-tetramethyluronium tetrafluoroborate, pyrrolidine and N,N-diisopropylethylamine in DMF to give the desired product as a light yellow solid (33%).

MS (TIC): 357.2 (M+H$^+$)

Intermediate

Lithium 1-tert-butoxycarbonyl-5-(1-isopropyl-piperidin-4-yloxy)-1H-pyrrolo 2,3-pyridine-2-carboxylate The title compound was synthesized in analogy to example 5, intermediate b), from 5-(1-isopropyl-piperidin-4-yloxy)-pyrrolo[2,3-b]pyridine-1,2-dicarboxylic acid 1-tert-butyl ester 2-ethyl ester (example 13, intermediate a)) and lithium hydroxide in water, methanol and tetrahydrofuran, to give the compound as a yellow solid (>100%).

MS (ISP): 404.4 (M+H$^+$)

Example 18

(4,4-Difluoro-piperidin-1-yl)-[5-(1-isopropyl-piperidin-4-yloxy)-1-methanesulfonyl-1H-pyrrolo[2,3-b]pyridin-2-yl]-methanone The suspension of 0.25 g (0.6 mmol) (4,4-difluoro-piperidin-1-yl)-[5-(1-isopropyl-piperidin-4-yloxy)-1H-pyrrolo[2,3-b]pyridin-2-yl]-methanone (example 13) and 30 mg (0.68 mmol; 55% dispersion in mineral oil) sodium hydride in 3 ml DMF was heated to 70° C. To the resulting solution 53 µl (77 mg, 0.67 mmol) methanesulfonyl chloride were added. After 1.5 h the heating bath was removed and the solution was poured on water and was extracted three times with ethyl acetate. The combined organic layers were washed with water and brine, dried over magnesium sulfate, filtered and evaporated. The crude product was purified by flash-chromatography on silica gel with dichloromethane:methanol:ammonia (9:1:0.1 v/v) to give 13 mg (44%) of the product as a light brown foam.

MS (TIC): 485.2 (M+H$^+$)

Example 19

(4,4-Difluoro-piperidin-1-yl)-{1-methanesulfonyl-5-[3-((S)-2-methyl-pyrrolidin-1-yl)-propoxy]-1H-pyrrolo[2,3-b]pyridin-2-yl}-methanone The title compound was synthesized in analogy to example 18 from (4,4-difluoro-piperidin-1-yl)-{5-[3-((S)-2-methyl-pyrrolidin-1-yl)-propoxy]-1H-pyrrolo[2,3-b]pyridin-2-yl}-methanone (example 11), sodium hydride and methanesulfonyl chloride, to give the desired product as a light yellow oil (52%).

MS (TIC): 485.3 (M+H$^+$)

Example 20

(4,4-Difluoro-piperidin-1-yl)-{1-methanesulfonyl-5-[3-((R)-2-methyl-pyrrolidin-1-yl)-propoxy]-1H-pyrrolo[2,3-b]pyridin-2-yl}-methanone The title compound was synthesized in analogy to example 18 from (4,4-difluoro-piperidin-1-yl)-{5-[3-((R)-2-methyl-pyrrolidin-1-yl)-propoxy]-1H-pyrrolo[2,3-b]pyridin-2-yl}-methanone (example 10)), sodium hydride and methanesulfonyl chloride, to give the desired product as a light yellow oil (53%).

MS (TIC): 485.3 (M+H$^+$)

Example 21

(4,4-Difluoro-piperidin-1-yl)-[5-(1-isopropyl-piperidin-4-yloxy)-1-(2-methoxy-ethyl)-1H-pyrrolo[2,3-b]pyridin-2-yl]-methanone The title compound was synthesized in analogy to example 18 from (4,4-difluoro-piperidin-1-yl)-[5-(1-isopropyl-piperidin-4-yloxy)-1H-pyrrolo[2,3-b]pyridin-2-yl]-methanone (example 13), sodium hydride and 2-bromoethyl methyl ether to give the desired product as light yellow oil (49%).

MS (TIC): 465.3 (M+H$^+$)

Example 22

(4,4-Difluoro-piperidin-1-yl)-[1-isopropyl-5-(1-isopropyl-piperidin-4-yloxy)-1H-pyrrolo[2,3-b]pyridin-2-yl]-methanone The title compound was synthesized in analogy to example 18 from (4,4-difluoro-piperidin-1-yl)-[5-(1-isopropyl-piperidin-4-yloxy)-1H-pyrrolo[2,3-b]pyridin-2-yl]-methanone (example 13), sodium hydride and 2-bromopropane, to give the desired product as a light brown foam (13%).

MS (TIC): 449.2 (M+H$^+$)

Example 23

[1-Cyclopropylmethyl-5-(1-isopropyl-piperidin-4-yloxy)-1H-pyrrolo[2,3-b]pyridin-2-yl]-(4,4-difluoro-piperidin-1-yl)-methanone The title compound was synthesized in analogy to example 18 from (4,4-difluoro-piperidin-1-yl)-[5-(1-isopropyl-piperidin-4-yloxy)-1H-pyrrolo[2,3-h]pyridin-2-yl]-methanone (example 13), sodium hydride and cyclopropylmethyl bromide, to give the desired product as a light brown oil (51%).

MS (TIC): 461.1 (M+H$^+$)

Example 24

[2-(4,4-Difluoro-piperidine-1-carbonyl)-5-(1-isopropyl-piperidin-4-yloxy)-pyrrolo[2,3-b]pyridin-1-yl]-acetonitrile The title compound was synthesized in analogy to example 18 from (4,4-difluoro-piperidin-1-yl)-[5-(1-isopropyl-piperidin-4-yloxy)-1H-pyrrolo[2,3-b]pyridin-2-yl]methanone (example 13), sodium hydride and bromoacetonitrile, to give the desired product as a light yellow oil (61%).

MS (TIC): 446.1 (M+H$^+$)

Example 25

(4,4-Difluoro-piperidin-1-yl)-[5-(1-isopropyl-piperidin-4-yloxy)-1-(2,2,2-trifluoro-ethyl)-1H-pyrrolo[2,3-b]pyridin-2-yl]-methanone The title compound was synthesized in analogy to example 18 from (4,4-difluoro-piperidin-1-yl)-[5-(1-isopropyl-piperidin-4-yloxy)-1H-pyrrolo[2,3-b]pyridin-2-yl]-methanone (example 13), sodium hydride and 2,2,2-trifluoroethyl methanesulfonate, to give the desired product as a yellow oil (48%).

MS (TIC): 489.2 (M+H$^+$)

Example 26

(4,4-Difluoro-piperidin-1-yl)-[1-(2-hydroxy-ethyl)-5-(1-isopropyl-piperidin-4-yloxy)-1H-pyrrolo[2,3-b]pyridin-2-yl]-methanone The solution of 55 mg (97 µmol) [1-[2-(tert-butyl-dimethyl-silanyloxy)-ethyl]-5-(1-isopropyl-piperidin-4-yloxy)-1H-pyrrolo[2,3-b]pyridin-2-yl]-(4,4-difluoro-piperidin-1-yl)-methanone was cooled down to 0° C. and 1 ml (1.49 g, 13 mmol) trifluoroacetic acid was added. The cooling bath was removed and stirring was continued for another hour at room temperature. The reaction was neutralized with 1M aqueous sodium hydroxide solution and extracted three times with dichloromethane. The combined organic layers were washed with brine, dried over magnesium sulfate, filtered and evaporated. The crude product was purified by flash-chromatography on silica gel with dichloromethane:methanol:ammonia (9:1:0.1 v/v) as eluant to give 29 mg (66%) of the product as a light yellow oil.

MS (TIC): 451.1 (M+H$^+$)

Intermediate

[1-[2-(tert-Butyl-dimethyl-silanyloxy)-ethyl]-5-(1-isopropyl-piperidin-4-yloxy)-1H-pyrrolo[2,3-b]pyridin-2-yl]-(4,4-difluoro-piperidin-1-yl)-methanone The title compound was synthesized in analogy to example 18 from (4,4-difluoro-piperidin-1-yl)-[5-(1-isopropyl-piperidin-4-yloxy)-1H-pyrrolo[2,3-b]pyridin-2-yl]methanone (example 13), sodium hydride and (2-bromoethoxy)-tert-butyldimethylsilane, to give the desired product as a light yellow solid (29%).

MS (TIC): 565.5 (M+H$^+$)

Example 27

(4,4-Difluoro-piperidin-1-yl)-[1-isopropyl-5-[3-((R)-2-methyl-pyrrolidin-1-yl)-propoxy]-1H-pyrrolo[2,3-b]pyridin-2-yl]-methanone The title compound was synthesized in analogy to example 18 from (4,4-difluoro-piperidin-1-yl)-{1-methanesulfonyl-5-[3-((R)-2-methyl-pyrrolidin-1-yl)-propoxy]-1H-pyrrolo[2,3-b]pyridin-2-yl}-methanone (example 20), sodium hydride and 2-bromopropane, to give the desired product as a colorless oil (26%).

MS (TIC): 449.2 (M+H$^+$)

Example 28

{1-Cyclopropylmethyl-5-[3-((R)-2-methyl-pyrrolidin-1-yl)-propoxy]-1H-pyrrolo[2,3-b]pyridin-2-yl}-(4,4-difluoro-piperidin-1-yl)-methanone The title compound was synthesized in analogy to example 18 from (4,4-difluoro-piperidin-1-yl)-{1-methanesulfonyl-5-[3-((R)-2-methyl-pyrrolidin-1-yl)-propoxy]-1H-pyrrolo[2,3-b]pyridin-2-yl}-methanone (example 20), sodium hydride and cyclopropylmethyl bromide, to give the desired product as a light yellow oil (53%).
MS (TIC): 461.4 (M+H$^+$)

Example 29

{2-(4,4-Difluoro-piperidine-1-carbonyl)-5-[3-((R)-2-methyl-pyrrolidin-1-yl)-propoxy]-pyrrolo[2,3-b]pyridin-1-yl}-acetonitrile The title compound was synthesized in analogy to example 18 from (4,4-difluoro-piperidin-1-yl)-{1-methanesulfonyl-5-[3-((R)-2-methyl-pyrrolidin-1-yl)-propoxy]-1H-pyrrolo[2,3-b]pyridin-2-yl}-methanone (example 20), sodium hydride and bromoacetonitrile, to give the desired product as a light yellow oil (3%).
MS (TIC): 446.3 (M+H$^+$)

Example 30

(4,4-Difluoro-piperidin-1-yl)-[5-[3-((R)-2-methyl-pyrrolidin-1-yl)-propoxy]-1-(2,2,2-trifluoroethyl)-1H-pyrrolo[2,3-b]pyridin-2-yl]-methanone The title compound was synthesized in analogy to example 18 from (4,4-difluoro-piperidin-1-yl)-{1-methanesulfonyl-5-[3-((R)-2-methyl-pyrrolidin-1-yl)-propoxy]-1H-pyrrolo[2,3-b]pyridin-2-yl}-methanone (example 20), sodium hydride and 2,2,2-trifluoroethyl methanesulfonate, to give the desired product as a light yellow oil (62%).
MS (TIC): 489.1 (M+H$^+$)

Example 31

[1-(4-Chloro-phenyl)-5-[3-((R)-2-methyl-pyrrolidin-1-yl)-propoxy]-1H-pyrrolo[2,3-b]pyridin-2-yl]-(4,4-difluoro-piperidin-1-yl)-methanone To the solution of 0.15 (0.37 mmol) (4,4-difluoro-piperidin-1-yl)-{1-methanesulfonyl-5-[3-((R)-2-methyl-pyrrolidin-1-yl)-propoxy]-1H-pyrrolo[2,3-b]pyridin-2-yl}-methanone (example 20) in 5 ml dichloromethane. 0.13 g (0.74 mmol) copper(II) acetate, 0.17 g (1.1 mmol) 4-chlorophenylboronic acid and 0.12 ml (0.12 mg, 1.5 mmol) pyridine were added and the suspension was stirred at room temperature for 18 hours. The solvent was evaporated and the residue was flash-chromatographed on silica gel with dichloromethane:methanol:ammonia (9:1:0.1 v/v) as eluant to give the compound as a light yellow solid (88%).
MS (TIC): 517.4 (M+H$^+$)

Example 32

[6-Chloro-5-(1-isopropyl-piperidin-4-yloxy)-1H-pyrrolo[2,3-b]pyridin-2-yl]-(4,4-difluoro-piperidin-1-yl)-methanone The title compound was synthesized in analogy to example 1 from 6-chloro-5-(1-isopropyl-piperidin-4-yloxy)-1H-pyrrolo[2,3-b]pyridine-2-carboxylic acid hydrochloride, O-(benzotriazol-1-yl)-N,N,N',N'-tetramethyluronium tetrafluoroborate, 4,4-difluoro-piperidine and N,N-diisopropylethylamine in DMF to give the desired product as a light yellow foam (40%).
MS (TIC): 441.2 (M+H$^+$)

Intermediates a) 5-Benzyloxy-7-oxy-pyrrolo[2,3-b]pyridine-1,2-dicarboxylic Acid 1-tert-butyl Ester 2-methyl Ester To the solution of 0.58 g (1.5 mmol) 5-benzyloxy-pyrrolo[2,3-b]pyridine-1,2-dicarboxylic acid 1-tert-butyl ester 2-methyl ester (intermediate H) in 6 ml dichloromethane 0.75 g (3.0 mmol; 70%) m-chloroperbenzoic acid was added. After 3 h, another 0.75 g m-chloroperbenzoic acid was added. After 18 hours the reaction was poured on 10% aqueous potassium carbonate solution and was extracted three times with dichloromethane. The combined organic layers were washed with brine, dried over magnesium sulfate, filtered and evaporated. The residue was stirred with ethyl acetate, filtered and dried under high vacuum to give 0.26 g (43%) of the desired product as a light yellow solid.
MS (ISP): 399.3 (M+H$^+$)

b) 5-Benzyloxy-6-chloro-pyrrolo[2,3-b]pyridine-1,2-dicarboxylic Acid 1-tert-butyl Ester 2-methyl Ester To the solution of 0.34 g (0.85 mmol) 5-benzyloxy-7-oxy-pyrrolo-[2,3-b]pyridine-1,2-dicarboxylic acid 1-tert-butyl ester 2-methyl ester in 5 ml tetrahydrofuran, 0.18 ml (0.14 g, 0.85 mmol) hexamethyldisilazane and 0.16 ml (0.20 g, 2.14 mmol) methyl chloroformate were added. After one hour another 0.16 ml methyl chloroformate were added and after 2 hours further-0.16 ml methyl chloroformate were added to drive the reaction to completeness. The solvent was evaporated and the residue chromatographed on silica gel with dichloromethane as eluant to give 0.22 g (61%) of the title compound as a white solid.
MS (EI): 416.1 (M), 316.1 (M-(CO$_2$+C$_4$H$_8$))

c) 6-Chloro-5-hydroxy-pyrrolo[2,3-b]pyridine-1,2-dicarboxylic Acid 1-tert-butyl Ester 2-methyl Ester The title compound was synthesized in analogy to example 9, intermediate b), through hydrogenation of 5-benzyloxy-6-chloro-pyrrolo[2,3-b]pyridine-1,2-dicarboxylic acid 1-tert-butyl ester 2-methyl ester to give the compound as a white solid (62%).
MS (EI): 326.3 (M), 226.0 (M-(CO$_2$+C$_4$H$_8$))

d) 6-Chloro-5-(1-isopropyl-piperidin-4-yloxy)-pyrrolo-[2,3-b]pyridine-1,2-dicarboxylic Acid 1-tert-butyl Ester 2-methyl Ester The title compound was synthesized in analogy to example 12, intermediate c), from 6-chloro-5-hydroxy-pyrrolo[2,3-b]pyridine-1,2-dicarboxylic acid 1-tert-butyl ester 2-methyl ester, triphenylphosphine and di-tert-butyl azodicarboxylate instead of diisopropyl azodicarboxylate, to give the compound as a light yellow foam (68%).
MS (TIC): 452.1 (M+H$^+$)

e) 6-Chloro-5-(1-isopropyl-piperidin-4-yloxy)-1H-pyrrolo[2,3-b]pyridine-2-carboxylic Acid Hydrochloride The title compound was synthesized in analogy to example 13, intermediate b), from 6-chloro-5-(1-isopropyl-piperidin-4-yloxy)-pyrrolo[2,3-b]pyridine-1,2-dicarboxylic acid 1-tert-butyl ester 2-methyl ester and concentrated hydrochloric acid in dioxan after stirring at reflux temperature for 4 hours. The product was obtained as a light brown solid (>100%).
MS (TIC): 336.2 (M–H)

Example 33

[6-Chloro-5-(1-isopropyl-piperidin-4-yloxy)-1-(2,2,2-trifluoro-ethyl)-1H-pyrrolo[2,3-b]pyridin-2-yl]-(4,4-difluoro-piperidin-1-yl)-methanone The title compound was synthesized in analogy to example 18 from 6-chloro-5-(1-isopropyl-piperidin-4-yloxy)-1H-pyrrolo[2,3-b]pyridine-2-carboxylic acid hydrochloride, sodium hydride and 2,2,2-trifluoroethyl methanesulfonate, to give the desired product as a light yellow oil (57%).
MS (TIC): 523.1 (M+H$^+$)

Example 34

[6-Chloro-1-cyclopropylmethyl-5-(1-isopropyl-piperidin-4-yloxy)-1H-pyrrolo[2,3-b]pyridin-2-yl]-(4,4-difluoro-piperidin-1-yl)-methanone The title compound was synthesized in analogy to example 18 from 6-chloro-5-(1 isopropyl-piperidin-4-yloxy)-1H-pyrrolo[2,3-b]pyridine-2-α-carboxylic acid hydrochloride, sodium hydride and cyclopropylmethyl bromide, to give the desired product as a light yellow oil (46%).
MS (TIC): 495.4 (M+H$^+$)

Intermediates

Intermediate A

5-Benzyloxy-6-chloro-pyrrolo[2,3-b]pyridine-1,2-dicarboxylic Acid 1-tert-butyl Ester 2-methyl Ester The solution of 17.2 g (91.0 mmol) 6-amino-5-bromo-pyridin-3-ol (prepared according to WO98/25920) in 175 ml DMF was cooled to 0° C. and treated in portions with 4.17 g (96.0 mmol; 55% dispersion in mineral oil) sodium hydride. Another 75 ml DMF were added and after 30 min. stirring at room temperature the mixture was cooled 10 to 0° C. and 11.4 ml (96.0 mmol) benzyl bromide were added dropwise. The cooling bath was removed and after 60 min. at room temperature the reaction mixture was poured on 10% aqueous ammonium chloride solution and was extracted three times with ethyl acetate. The combined organic layers were washed with water and brine, dried over magnesium sulfate and evaporated. The crude product was purified by flash column chromatography with n-heptane:ethyl acetate (1:1 v/v) as eluant. The suspension formed during evaporation was filtered and the filter cake was washed with n-heptane to give 16.2 g (63%) of the product as a colorless solid. The remaining pale yellow mother liquor contained another 4.2 g (16%) of the product which were pure enough for the next step.
MS (EI): 278.0; 280.0 (M)

Intermediate B

5-Benzyloxy-[3-[3-[dimethyl-(1,1,2-trimethyl]-propyl)-silanyloxy]-prop-1-ynyl]-pyridine-2-ylamine The mixture of 0.29 g (1.54 mmol) copper iodide and bis(triphenylphosphine) palladium(II) chloride in 215 ml triethylamine were stirred 15 min. under reflux. The mixture was cooled to 40° C., then 21.5 g (77.0 mmol) 5-benzyloxy-6-chloro-pyrrolo[2,3-b]pyridine-1,2-dicarboxylic acid 1-tert-butyl ester 2-methyl ester and 18.6 g (94.0 mmol) dimethyl-prop-2-ynyloxy-(1,1,2-trimethyl-propyl)-silane were added and the reaction mixture was refluxed for 19 h. After cooling down to room temperature the suspension was poured on 10% aqueous citric acid solution and extracted three times with ethyl acetate. The combined organic layers were washed with brine, dried over magnesium sulfate and evaporated. The residue was flash-chromatographed on silica gel with acetone:n-heptane (1:2 v/v) as eluant to give 13.7 g (45%) of the product as brown solid together with some not reacted starting material (ca 8.7 g) which could be used again for the same reaction.
MS (EI): 396.3 (M); 311.1 (M–$C_6H_{13}$)

Intermediate C

5-Benzyloxy-2-[dimethyl-(1,1,2-trimethyl-propyl)-silanyloxymethyl]-1H-pyrrolo[2,3-b]pyridine The solution of 1.0 g (2.5 mmol) 5-benzyloxy-3-{3-[dimethyl-(1,1,2-trimethyl-propyl)-silanyloxy]-prop-1-ynyl}-pyridin-2-ylamine in 25 ml dichloromethane at 0° C. was treated with 0.39 ml (0.58 g, 1.10 mmol) trifluoroacetic anhydride. The cooling bath was removed and after stirring for 60 min. at room temperature the volatile components were removed at a rotary evaporator. The remaining light brown oil was dissolved in 25 ml triethylamine and 14 mg (73.5 μmol) copper (I) iodide and 18 mg (25.6 μmol) bis(triphenylphosphine) palladium(II) chloride were added and the mixture was stirred at reflux temperature for 20 h. The mixture was poured on 10% aqueous ammonium chloride solution and extracted three times with ethyl acetate. The combined organic layers were washed with water and brine, dried over magnesium sulfate, filtered and evaporated. The crude product was purified by flash chromatography with acetone:n-heptane (1:3 v/v) as eluant to give 0.5 g (45%) of the desired compound as a yellow solid.
MS (EI): 396.2 (M); 311.1 (M-$C_6H_{13}$)

Intermediate D (5-Benzyloxy-1H-pyrrolo[2,3-b]pyridin-2-yl)-methanol

To the solution of 0.53 g (1.3 mmol) 5-benzyloxy-2-[dimethyl-(1,1,2-trimethyl-propyl)-silanyloxymethyl]-1H-pyrrolo[2,3-b]pyridine in 3 ml tetrahydrofuran 1.6 ml (1.6 mmol) tetra-n-butylammonium fluoride (1M solution in THF) were added. After 75 min. the solution was poured on saturated aqueous sodium bicarbonate solution and was extracted three times with ethyl acetate. The combined organic layers were washed with brine, dried over magnesium sulfate, filtered and evaporated. The residue was stirred in tert-butyl methyl ether, filtered and washed with tert-butyl methyl ether to give 0.3 g (88%) of the product as a brown solid.
MS (EI): 254.1 (M)

Intermediate E

5-Benzyloxy-1H-pyrrolo[2,3-b]pyridine-2-carbaldehyde

The suspension of 0.3 g (1.2 mmol) (5-benzyloxy-1H-pyrrolo[2,3-b]pyridin-2-yl)-methanol and 0.82 g (9.4 mmol) manganese dioxide in 15 ml dichloromethane was stirred 3 h at room temperature. After filtration over dicalite speed plus® (Aldrich) the solvent was evaporated to give 0.22 g (74%) of the desired compound as a light brown solid.

MS (EI): 252.1 (M)

Intermediate F

5-Benzyloxy-2-formyl-pyrrolo[2,3-b]pyridine-1-carboxylic Acid tert-butyl Ester To the suspension of 0.42 g (1.7 mmol) 5-benzyloxy-1H-pyrrolo[2,3-b]pyridine-2-carbaldehyde in 10 ml dichloromethane 0.38 g (1.75 mmol) di-tert-butyl dicarbonate and 10 mg (82 µmol) 4-(dimethylamino)pyridine were added. After 20 min. a solution had formed which was evaporated. The residue was flash-chromatographed on silica gel with n-heptane:ethyl acetate (2:1 v/v). Upon evaporation a suspension formed which was cooled to 5° C. and filtered. The filter cake was washed with n-heptane and dried under vacuum to give 0.4 g (69%) of the product as a light brown solid.

MS (EI): 352.1 (M); 252.1 (M-($C_4H+CO_2$))

Intermediate G

5-Benzyloxy-pyrrolo[2,3-b]pyridine-1,2-dicarboxylic Acid 1-tert-butyl Ester

To the solution of 0.41 g (1.2 mmol) 5-benzyloxy-2-formyl-pyrrolo[2,3-b]pyridine-1-carboxylic acid tert-butyl ester in 10 ml tert-butanol, 7 ml 2-methyl-2-butene and 20 ml acetonitrile, a mixture consistent of 1.2 g (10.6 mmol; 80%) sodium chlorite and 0.97 g (8.1 mmol) sodium dihydrogen phosphate in 10 ml water was added dropwise. The resulting two-phase mixture was stirred 1.5 h at room temperature. Then the organic components were evaporated at a rotary evaporator and the remaining aqueous phase was extracted three times with dichloromethane. The combined organic layers were washed with 10% aqueous sodium thiosulfate solution and brine, dried over magnesium sulfate, filtered and evaporated. The crude product was purified by flash-chromatography on silica gel with ethyl acetate:n-heptane (1:1 v/v) as eluant to give 0.35 g (74%) of the compound as a yellow foam.

MS (TIC): 367.1 (M−H)

Intermediate H

5-Benzyloxy-pyrrolo[2,3-b]pyridine-1,2-dicarboxylic Acid 1-tert-butyl Ester 2-methyl Ester The solution of 0.2 g (0.54 mmol) 5-benzyloxy-pyrrolo[2,3-b]pyridine-1,2-dicarboxylic acid 1-tert-butyl ester in 2 ml DMF was cooled down to 0° C. and 26 mg (0.54 mmol; 55% dispersion in mineral oil) were added. After 15 min., 38 µl (85 mg, 0.6 mmol) methyl iodide were added and the cooling bath was removed. After 5 hours the reaction mixture was poured on water and was extracted five times with dichloromethane. The organic layers were dried over magnesium sulfate, filtered and evaporated to give 0.19 g (93%) the compound as a light yellow oil which was pure enough for the preceding steps without further purification.

MS (TIC): 383.0 (M+$H^+$)

Intermediate J

5-Benzyloxy-1H-pyrrolo[2,3-b]pyridine-2-carboxylic Acid Methyl Ester

The suspension of 0.2 g (0.54 mmol) 5-benzyloxy-pyrrolo[2,3-b]pyridine-1,2-dicarboxylic acid 1-tert-butyl ester (intermediate G) and 30 µl of concentrated sulfuric acid in 2 ml methanol was heated under reflux. After 1.5 h another 2 ml methanol and 30 µl of concentrated sulfuric acid were added. The resulting clear solution was refluxed 3 hours and after cooling down to room temperature was poured on saturated sodium bicarbonate solution and extracted three times with ethyl acetate. The combined organic layers were washed with brine, dried over magnesium sulfate, filtered and evaporated to give 0.12 g (78%) of the product as a colorless solid.

MS (TIC): 282.8 (M+$H^+$)

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The invention claimed is:
1. Compounds of the general formula

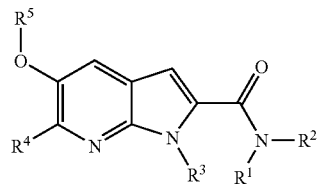

wherein
$R^1$ is selected from the group consisting of:
lower alkyl, lower alkenyl, lower alkinyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy and lower hydroxyalkyl,
lower phenylalkyl wherein the phenyl ring may be unsubstituted or substituted with one or two groups independently selected from lower alkyl, halogen, lower alkoxy and lower hydroxyalkyl,
lower heteroarylalkyl wherein the heteroaryl ring may be unsubstituted or substituted with one or two groups independently selected from lower alkyl, halogen, lower alkoxy and lower hydroxyalkyl, and
lower heterocyclylalkyl wherein the heterocyclyl ring may be unsubstituted or substituted with one or two lower alkyl groups;
$R^2$ is selected from the group consisting of hydrogen lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy and lower hydroxyalkyl,
lower phenylalkyl wherein the phenyl ring may be unsubstituted or substituted with one or two groups independently selected from lower alkyl, halogen, lower alkoxy and lower hydroxyalkyl,
lower heteroarylalkyl wherein the heteroaryl ring may be unsubstituted or substituted with one or two groups independently selected from lower alkyl, halogen, lower alkoxy and lower hydroxyalkyl, and
lower heterocyclylalkyl wherein the heterocyclyl ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group,
said saturated or partly unsaturated heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen;

$R^3$ is selected from the group consisting of hydrogen, lower alkyl, lower hydroxyalkyl, lower alkoxyalkyl, lower halogenalkyl, lower cycloalkylalkyl, lower alkanoyl, lower cyanoalkyl, lower alkylsulfonyl, phenylsulfonyl wherein the phenyl ring may be unsubstituted or substituted with one or two groups independently selected from lower alkyl, halogen, lower alkoxy lower halogenalkoxy and lower hydroxyalkyl;

phenyl unsubstituted or substituted with one or two groups independently selected from lower alkyl, halogen, lower alkoxy, lower halogenalkoxy and lower hydroxyalkyl; lower phenylalkyl, wherein the phenyl ring may be unsubstituted or substituted with one or two groups independently selected from lower alkyl, halogen, lower alkoxy, lower halogenalkoxy and lower hydroxyalkyl; and lower alkyl or halogen;

$R^4$ is hydrogen or halogen;

$R^5$ is a group selected from

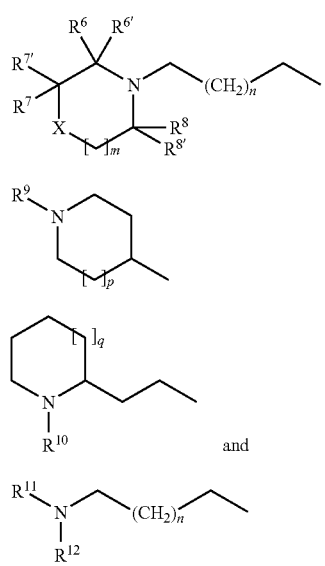

wherein m is 0, 1 or 2;

n is 0, 1 or 2;

X is selected from $CR^{13}R^{13'}$, O and S;

$R^6, R^{6'}, R^7, R^{7'}, R^8, R^{8'}, R^{13}$ and $R^{13'}$ independently from each other are selected from the group consisting of hydrogen, lower alkyl, hydoxy, halogen and dialkylamino, or $R^7$ and $R^{13}$ together form a double bond;

p is 0, 1 or 2;

$R^9$ is selected from lower alkyl, cycloalkyl, lower cycloalkylalkyl and lower phenylalkyl;

q is 0, 1 or 2;

$R^{10}$ is lower alkyl;

$R^{11}$ is lower alkyl;

$R^{12}$ is lower alkyl;

and pharmaceutically acceptable salts thereof.

2. Compounds of formula I according to claim 1, wherein $R^1$ is selected from the group consisting of lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenalkoxy or lower hydroxyalkyl, lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl, and lower heterocyclylalkyl wherein the heterocycly ring may be unsubstituted or substituted with one or two lower alkyl groups, and $R^2$ is hydrogen or lower alkyl.

3. Compounds of formula I according to claim 1, wherein $R^1$ is lower phenylalkyl wherein the phenyl ring may be unsubstituted or substituted with one or two groups independently selected from lower alkyl, halogen, lower alkoxy or lower hydroxyalkyl, and $R^2$ is hydrogen or lower alkyl.

4. Compounds of formula I according to claim 1, wherein $R^1$ and $R^2$ are lower alkyl.

5. Compounds of formula I according to claim 1, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group, said saturated or partly unsaturated heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

6. Compounds of formula I according to claim 1, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two or three groups independently selected from lower alkyl, halogen, halogenalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

7. Compounds of formula I according to 1, wherein $R^1$ and $R^2$ together with the nitrogen atom to which they are attached form a heterocyclic ring selected from the group consisting of morpholine, piperidine, 4,4-difluoropiperidine and pyrrolidine.

8. Compounds of formula I according to claim 1, wherein $R^3$ is selected from the group consisting of hydrogen, lower alkyl, lower hydroxyalkyl, lower alkoxyalkyl, lower halogenalkyl, lower cycloalkylalkyl, lower cyanoalkyl, lower alkylsulfonyl, and phenyl unsubstituted or substituted with one or two groups independently selected from lower alkyl, halogen, lower alkoxy, lower halogenalkoxy and lower hydroxyalkyl.

9. Compounds of formula I according to claim 1, wherein $R^3$ is selected from the group consisting of hydrogen, lower alkyl, lower halogenalkyl, lower cycloalkylalkyl and lower cyanoalkyl.

10. Compounds of formula I according to claim 1, wherein $R^3$ is hydrogen.

11. Compounds of formula I according to claim 1, wherein $R^4$ is hydrogen.

12. Compounds of formula I according to claim 1, wherein $R^4$ is chloro or bromo.

13. Compounds of formula I according to claim 1, wherein $R^5$ signifies

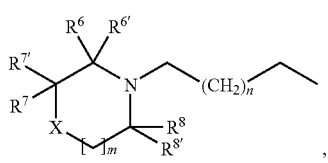

Het 1 wherein m is 0, 1 or 2; n is 0, 1 or 2; X is selected from $CR^{13}R^{13'}$, O and S; and $R^6$, $R^{6'}$, $R^7$, $R^{7'}$, $R^8$, $R^{8'}$, $R^{13}$ and $R^{13'}$ independently from each other are selected from the group consisting of hydrogen, lower alkyl, hydroxy, halogen and dialkylamino, or $R^7$ and $R^{13}$ together form a double bond.

14. Compounds of formula I according to claim 1, wherein m is 0 or 1, n is 1, X is $CR^{13}R^{13'}$ and $R^6$, $R^{6'}$, $R^7$, $R^{7'}$, $R^8$, $R^{8'}$, $R^{13}$ and $R^{13'}$ are hydrogen or lower alkyl.

15. Compounds of formula I according to claim 1, wherein $R^5$ signifies

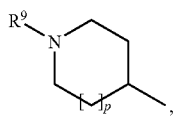

Het 2 wherein p is 0, 1 or 2, and $R^9$ is selected from lower alkyl, cycloalkyl, lower cycloalkylalkyl and lower phenylalkyl.

16. Compounds of formula I according to claim 1, wherein $R^9$ is lower alkyl.

17. Compounds of formula I according to claim 1, wherein $R^9$ is cycloalkyl.

18. Compounds of formula I according to claim 1 to 17, wherein p is 1.

19. Compounds of formula I according to claim 1, wherein $R^5$ signifies

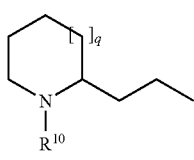

Het 3 wherein q is 0, 1 or 2; and $R^{10}$ is lower alkyl.

20. Compounds of formula I according to claim 1, wherein $R^5$ signifies

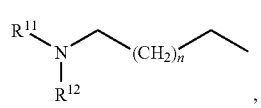

Het 4 wherein n is 0, 1 or 2, $R^{11}$ is lower alkyl and $R^{12}$ is lower alkyl.

21. Compounds of formula I according to claim 1, selected from the group consisting of morpholin-4-yl-[5-(3-piperidin-1-yl-propoxy)-1H-pyrrolo[2,3-b]pyridin-2-yl]-methanone, piperidin-1-yl-[5-(3-piperidin-1-yl-propoxy)-1H-pyrrolo[2,3-b]pyridin-2-yl]-methanone,

[5-(3-piperidin-1-yl-propoxy)-1H-pyrrolo[2,3-b]-pyridin-2-yl]-pyrrolidin-1-yl-methanone, 5-(3-piperidin-1-yl-propoxy)-1H-pyrrolo[2,3-b]-pyridine-2-carboxylic acid 4-fluoro-benzylamide, morpholin-4-yl-[5-(3-pyrrolidin-1-yl-propoxy)-1H-pyrrolo[2,3-b]pyridin-2-yl]-methanone, piperidin-1-yl-[5-(3-pyrrolidin-1-yl-propoxy)-1H-pyrrolo[2,3-b]pyridin-2-yl]-methanone, pyrrolidin-1-yl-[5-(3-pyrrolidin-1-yl-propoxy)-1H-pyrrolo[2,3-b]pyridin-2-yl]-methanone, 5-(3-pyrrolidin-1-yl-propoxy)-1H-pyrrolo[2,3-b]-pyridine-2-carboxylic acid 4-fluoro-benzylamide, (4,4-difluoro-piperidin-1-yl)-{5-[3-((2R,5R)-2,5-dimethyl-pyrrolidin-1-yl)-propoxy]-1H-pyrrolo[2,3-b]pyridin-2-yl}-methanone, (4,4-difluoro-piperidin-1-yl)-{5-[3-((R)-2-methyl-pyrrolidin-1-yl)-propoxy]-1H-pyrrolo[2,3-b]pyridin-2-yl}-methanone, (4,4-difluoro-piperidin-1-yl)-{5-[3-((S)-2-methyl-pyrrolidin-1-yl)-propoxy]-1H-pyrrolo[2,3-b]pyridin-2-yl}-methanone,

[5-(1-cyclopropyl-piperidin-4-yloxy)-1H-pyrrolo[2,3-b]-pyridin-2-yl]-morpholin-4-yl-methanone, (4,4-difluoro-piperidin-1-yl)-[5-(1-isopropyl-piperidin-4-yloxy)-1H-pyrrolo[2,3-b]pyridin-2-yl]-methanone, 5-(1-isopropyl-piperidin-4-yloxy)-1H-pyrrolo[2,3-b]-pyridine-2-carboxylic acid 4-fluoro-benzylamide,

[5-(1-isopropyl-piperidin-4-yloxy)-1H-pyrrolo[2,3-b]-pyridin-2-yl]-piperidin-1-yl-methanone,

[5-(1-isopropyl-piperidin-4-yloxy)-1H-pyrrolo[2,3-b]-pyridin-2-yl]-morpholin-4-yl-methanone,

[5-(1-isopropyl-piperidin-4-yloxy)-1H-pyrrolo[2,3-b]-pyridin-2-yl]-pyrrolidin-1-yl-methanone, (4,4-difluoro-piperidin-1-yl)-[5-(1-isopropyl-piperidin-4-yloxy)-1-methanesulfonyl-1H-pyrrolo[2,3-b]pyridin-2-yl]-methanone, (4,4-difluoro-piperidin-1-yl)-{1-methanesulfonyl-5-[3-((S)-2-methyl-pyrrolidin-1-yl)-propoxy]-1H-pyrrolo[2,3-b]pyridin-2-yl}-methanone, (4,4-difluoro-piperidin-1-yl)-{1-methanesulfonyl-5-[3-((R)-2-methyl-pyrrolidin-1-yl)-propoxy]-1H-pyrrolo-[2,3-b]pyridin-2-yl}-methanone, (4,4-difluoro-piperidin-1-yl)-[5-(1-isopropyl-piperidin-4-yloxy)-1-(2-methoxy-ethyl)-1H-pyrrolo[2,3-b]pyridin-2-yl]-methanone, (4,4-difluoro-piperidin-1-yl)-[1-isopropyl-5-(1-isopropyl-piperidin-4-yloxy)-1H-pyrrolo[2,3-b]pyridin-2-yl]-methanone,

[1-cyclopropylmethyl-5-(1-isopropyl-piperidin-4-yloxy)-1H-pyrrolo[2,3-b]pyridin-2-yl]-(4,4-difluoro-piperidin-1-yl)-methanone,

[2-(4,4-difluoro-piperidine-1-carbonyl)-5-(1-isopropyl-piperidin-4-yloxy)-pyrrolo[2,3-b]pyridin-1-yl]-acetonitrile, (4,4-difluoro-piperidin-1-yl)-[5-(1-isopropyl-piperidin-4-yloxy)-1-(2,2,2-trifluoro-ethyl)-1H-pyrrolo[2,3-b]pyridin-2-yl]-methanone, (4,4-difluoro-piperidin-1-yl)-[1-(2-hydroxy-ethyl)-5-(1-isopropyl-piperidin-4-yloxy)-1H-pyrrolo[2,3-b]pyridin-2-yl]-methanone, (4,4-difluoro-piperidin-1-yl)-{1-isopropyl-5-[3-((R)-2-methyl-pyrrolidin-1-yl)-propoxy]-1H-pyrrolo[2,3-b]pyridin-2-yl}-methanone, {1-cyclopropylmethyl-5-[3-((R)-2-methyl-pyrrolidin-1-yl)-propoxy]-1H-pyrrolo[2,3-b]pyridin-2-yl}-(4,4-difluoro-piperidin-1-yl)-methanone, {2-(4,4-difluoro-piperidine-1-carbonyl)-5-[3-((R)-2-methyl-pyrrolidin-1-yl)-propoxy]-pyrrolo[2,3-b]pyridin-1-yl}-acetonitrile, (4,4-difluoro-piperidin-1-yl)-[5-[3-((R)-2-methyl-pyrrolidin-1-yl)-propoxy]-1-(2,2,2-trifluoro-ethyl)-1H-pyrrolo[2,3-b]pyridin-2-yl]-methanone, {1-(4-chloro-phenyl)-5-[3-((R)-2-methyl-pyrrolidin-1-yl)-propoxy]-1H-pyrrolo[2,3-b]pyridin-2-yl}-(4,4-difluoro-piperidin-1-yl)-methanone,

[6-chloro-5-(1-isopropyl-piperidin-4-yloxy)-1H-pyrrolo[2,3-b]pyridin-2-yl]-(4,4-difluoro-piperidin-1-yl)-methanone,

[6-chloro-5-(1-isopropyl-piperidin-4-yloxy)-1-(2,2,2-trifluoro-ethyl)-1H-pyrrolo[2,3-b]pyridin-2-yl]-(4,4-difluoro-piperidin-1-yl)-methanone,

[6-chloro-1-cyclopropylmethyl-5-(1-isopropyl-piperidin-4-yloxy)-1H-pyrrolo[2,3-b]pyridin-2-yl]-(4,4-difluoro-piperidin-1-yl)-methanone, and pharmaceutically acceptable salts thereof.

22. Compounds of formula I according to claim 1, selected from the group consisting of (4,4-difluoro-piperidin-1-yl)-{5-[3-((R)-2-methyl-pyrrolidin-1-yl)-propoxy]-1H-pyrrolo[2,3-b]pyridin-2-yl}-methanone, (4,4-difluoro-piperidin-1-yl)-[5-(1-isopropyl-piperidin-4-yloxy)-1H-pyrrolo[2,3-b]pyridin-2-yl]-methanone, (4,4-difluoro-piperidin-1-yl)-[1-isopropyl-5-(1-isopropyl-piperidin-4-yloxy)-1H-pyrrolo[2,3-b]pyridin-2-yl]-methanone,

[1-cyclopropylmethyl-5-(1-isopropyl-piperidin-4-yloxy)-1H-pyrrolo[2,3-b]pyridin-2-yl]-(4,4-difluoro-piperidin-1-yl)-methanone,

[2-(4,4-difluoro-piperidine-1-carbonyl)-5-(1-isopropyl-piperidin-4-yloxy)-pyrrolo[2,3-b]pyridin-1-yl]-acetonitrile,

[6-chloro-5-(1-isopropyl-piperidin-4-yloxy)-1H-pyrrolo[2,3-b]pyridin-2-yl]-(4,4-difluoro-piperidin-1-yl)-methanone,

[6-chloro-5-(1-isopropyl-piperidin-4-yloxy)-1-(2,2,2-trifluoro-ethyl)-1H-pyrrolo[2,3-b]pyridin-2-yl]-(4,4-difluoro-piperidin-1-yl)-methanone,

[6-chloro-1-cyclopropylmethyl-5-(1-isopropyl-piperidin-4-yloxy)-1H-pyrrolo[2,3-b]pyridin-2-yl]-(4,4-difluoro-piperidin-1-yl)-methanone, and pharmaceutically acceptable salts thereof.

23. A process for the manufacture of compounds according to claim 1 which process comprises a) reacting a compound of the formula II

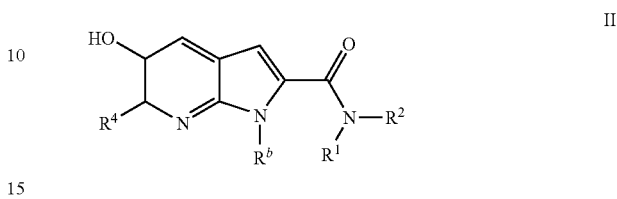

wherein $R^1$, $R^2$ and $R^4$ are as defined in claim 1 and $R^b$ is hydrogen or tert-butoxycarbonyl, with an alcohol of the formula III

HO—$R^5$     III wherein $R^5$ is as defined in claim 1, in the presence of a trialkylphosphine or triphenylphosphine and of an azo compound to obtain a compound of the formula IA

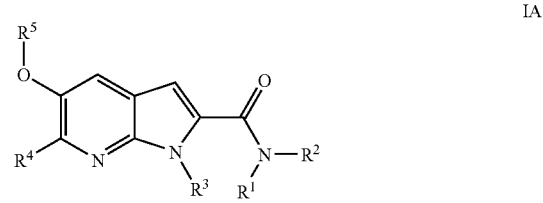

wherein $R^3$ is hydrogen, and optionally transferring into a compound of formula IB

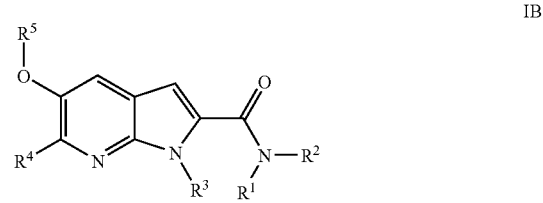

wherein $R^3$ is a group as defined in claim 1 other than hydrogen, and if desired, converting the compound obtained into a pharmaceutically acceptable acid addition salt, or alternatively, b) coupling a compound of formula IV

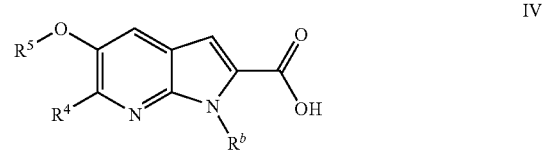

wherein $R^4$ and $R^5$ are as defined in claim 1 and $R^b$ is hydrogen or tert-butoxycarbonyl, with an amine of the formula V $$H\text{—}NR^1R^2 \qquad V$$

wherein $R^1$ and $R^2$ are as defined in claim 1, under basic conditions to obtain a compound of the formula IA

*[Chemical structure IA: a pyrrolopyridine with $R^5O$—, $R^4$—, ring nitrogen, and a carboxamide group $C(O)N(R^1)(R^2)$ at the 2-position, with $R^3$ on the pyrrole nitrogen]* wherein $R^3$ is hydrogen, and optionally transferring into a compound of formula IB

*[Chemical structure IB: same core as IA]* wherein $R^3$ is a group as defined herein before other than hydrogen, and if desired, converting the compound obtained into a pharmaceutically acceptable acid addition salt.

24. A pharmaceutical composition, comprising a therapeutically effective amount of a compound according to claim 1 as well as a pharmaceutically acceptable carrier and/or adjuvant.

\* \* \* \* \*